(12) United States Patent
Aljure

(10) Patent No.: US 11,839,713 B2
(45) Date of Patent: Dec. 12, 2023

(54) METHOD AND APPARATUS FOR EMULSIFYING TISSUE

(71) Applicant: REVELA MEDICAL, INC., Ithaca, NY (US)

(72) Inventor: Alfonso Aljure, Bogota (CO)

(73) Assignee: REVELA MEDICAL, INC., Ithaca, NY (US)

( * ) Notice: Subject to any disclaimer, the term of this patent is extended or adjusted under 35 U.S.C. 154(b) by 0 days.

(21) Appl. No.: 17/784,504

(22) PCT Filed: Dec. 10, 2020

(86) PCT No.: PCT/US2020/064273
§ 371 (c)(1),
(2) Date: Jun. 10, 2022

(87) PCT Pub. No.: WO2021/119286
PCT Pub. Date: Jun. 17, 2021

(65) Prior Publication Data
US 2023/0028334 A1    Jan. 26, 2023

Related U.S. Application Data

(60) Provisional application No. 62/954,628, filed on Dec. 29, 2019, provisional application No. 62/946,112, filed on Dec. 10, 2019.

(51) Int. Cl.
*A61M 1/00* (2006.01)
*A61B 17/32* (2006.01)

(52) U.S. Cl.
CPC ............. *A61M 1/772* (2021.05); *A61M 1/76* (2021.05); *A61M 1/89* (2021.05); *A61B 2017/32007* (2017.08)

(58) Field of Classification Search
CPC .......... A61M 1/772; A61M 1/89; A61M 1/76; A61B 2017/32007
USPC ......................................................... 604/542
See application file for complete search history.

(56) References Cited

U.S. PATENT DOCUMENTS

| | | | | |
|---|---|---|---|---|
| 4,808,154 A | * | 2/1989 | Freeman | A61F 9/00745 604/22 |
| 4,886,491 A | * | 12/1989 | Parisi | A61N 7/00 604/902 |
| 5,112,302 A | | 5/1992 | Cucin | |
| 5,244,458 A | * | 9/1993 | Takasu | A61M 1/79 604/902 |

(Continued)

OTHER PUBLICATIONS

For PCT/US2020/064273 filed Dec. 10, 2020: International Search Report dated Mar. 1, 2021 Written Opinion dated Apr. 1, 2021.

(Continued)

*Primary Examiner* — Andrew J Mensh
(74) *Attorney, Agent, or Firm* — Paul D. Bianco; Fleit Intellectual Property Law

(57) ABSTRACT

A method and apparatus that reduces the time and trauma associated with tissue removal procedures such as Ultrasound Assisted Liposuction, which emulsifies and then extracts unwanted adipose from a patient's target zone. Emulsification and suction are optimized and performed in a synchronous manner by a single apparatus to improve the outcome and minimize, if not eliminate, the limitations, risks and complications caused by current state of the art techniques.

20 Claims, 9 Drawing Sheets

(56) References Cited

U.S. PATENT DOCUMENTS

| | | | |
|---|---|---|---|
| 5,419,761 A * | 5/1995 | Narayanan | A61B 17/22012 604/22 |
| 5,447,494 A | 9/1995 | Dorsey | |
| 5,527,273 A | 6/1996 | Manna | |
| 6,102,885 A * | 8/2000 | Bass | A61B 18/04 604/35 |
| 6,368,299 B1 | 4/2002 | Cimiino | |
| 6,379,326 B1 | 4/2002 | Cimino | |
| 2020/0038242 A1 * | 2/2020 | Nallakrishnan | A61F 9/00754 |

OTHER PUBLICATIONS

For PCT/US2020/064273 filed Dec. 10, 2020: International Preliminary Report on Patentability with Written Opinion dated May 17, 222.

* cited by examiner

Fig 1
(Prior Art)
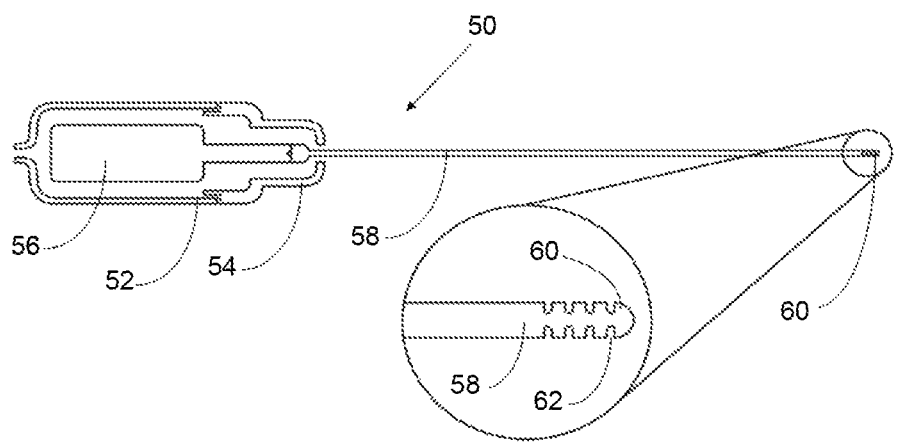
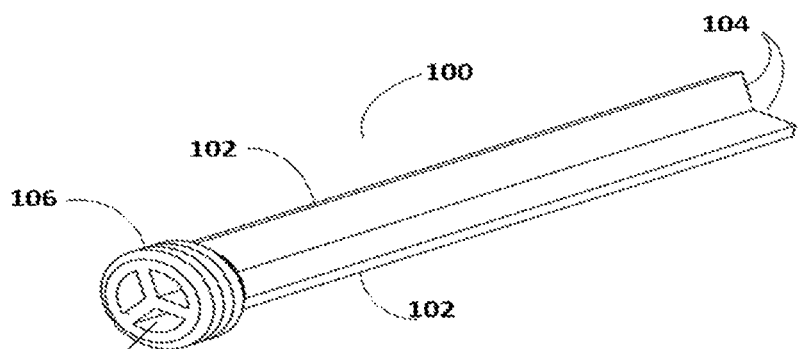
Fig 2
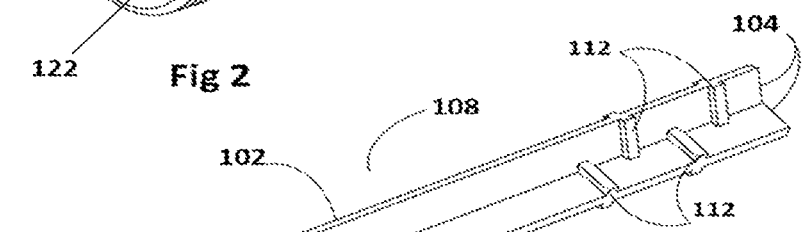
Fig 3
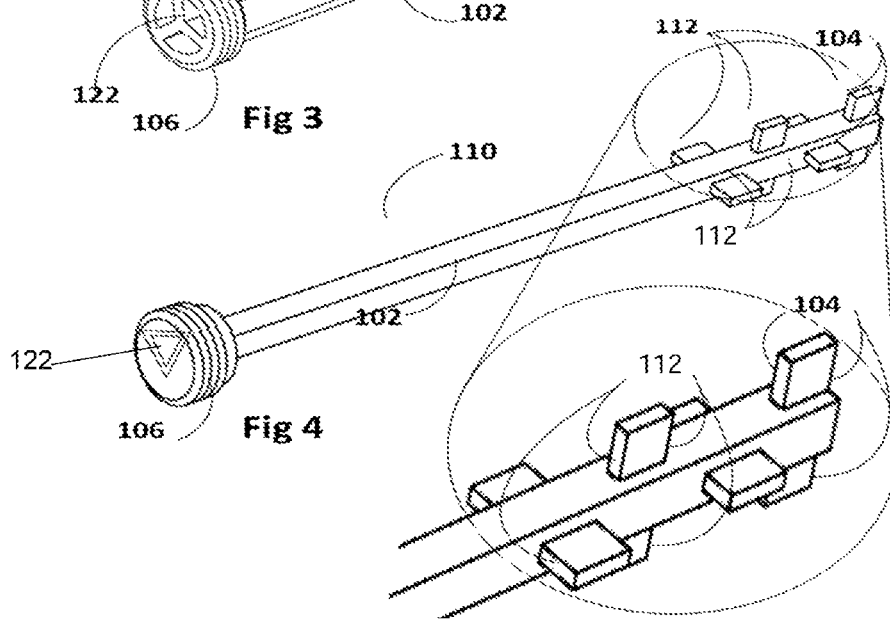
Fig 4

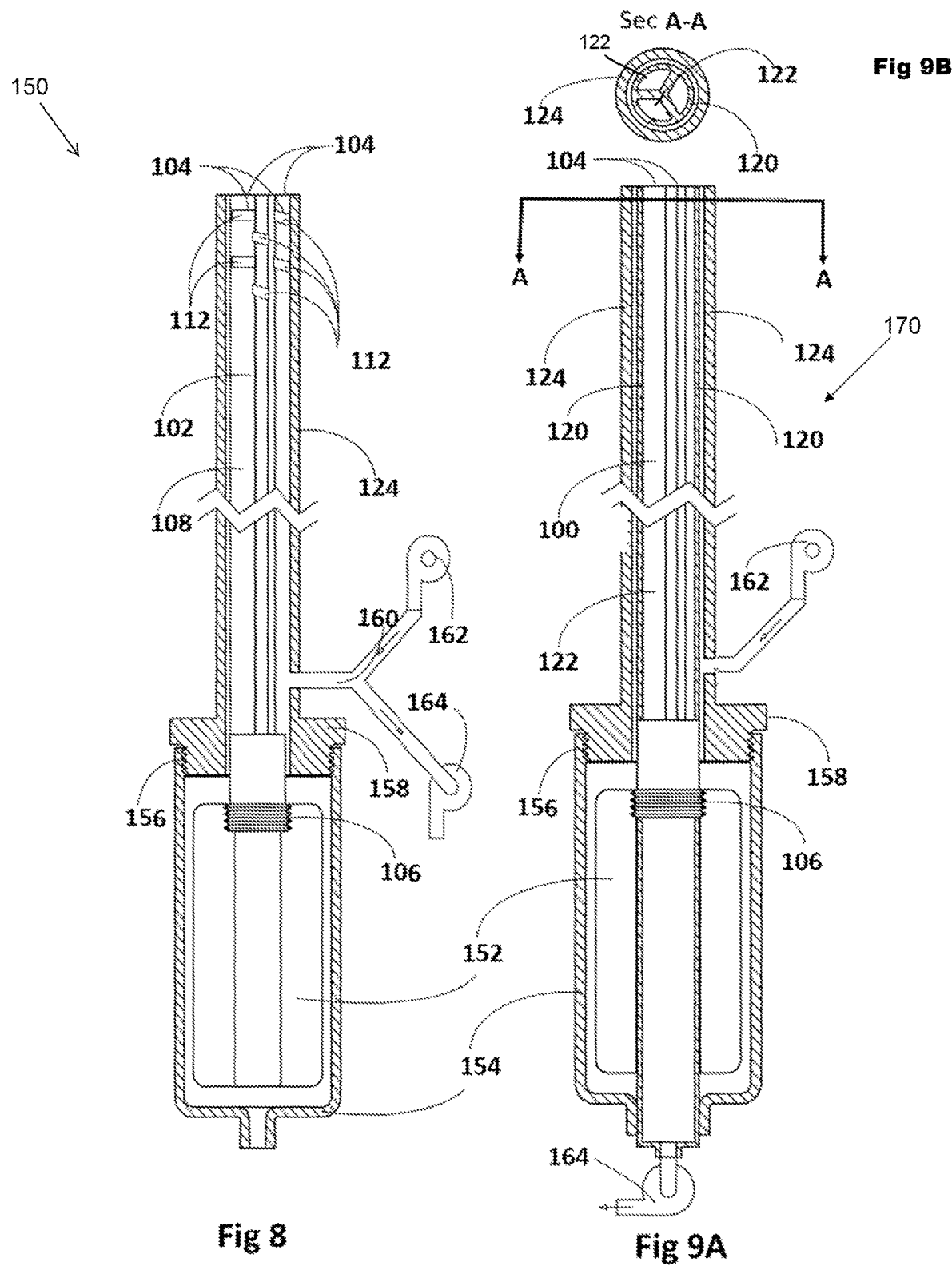

METHOD AND APPARATUS FOR EMULSIFYING TISSUE

CROSS REFERENCE TO RELATED APPLICATIONS

This disclosure relates to and claims priority to U.S. Provisional Patent Application No. 62/946,112 filed Dec. 10, 2019 and U.S. Provisional Patent Application No. 62/954,628 filed Dec. 29, 2019. The entire contents of each of the above-identified patent applications are hereby incorporated by reference herein.

FIELD OF THE DISCLOSURE

Although the disclosed apparatus and method can be used to simultaneously fragment and extract any kind of soft or hard tissue from a living or dead body, the disclosure focusses primarily on the extraction of unwanted adipose tissue from a patient's target zone in a plastic surgery procedure known as Ultrasound Assisted Liposuction.

BACKGROUND

The removal of unwanted adipose tissue from the human body (lipoplasty) dates back over one hundred years and has been the subject of many efforts to improve the procedure and outcome and minimize complications. In the late 1960's European techniques to literally cut away fat with instruments called curettes and large incisions, were used but limited to small areas given the amount of bleeding it caused.

The concept of using a cannula attached to a suction pump (liposuction) started in the 1970's with the creation of the suction cannula for a Suction Assisted Liposuction (SAL) protocol.

This liposuction technique was optimized by a method in which both lidocaine, for anesthesia, and epinephrine, a drug that shrinks capillaries to reduce bleeding, were added to the irrigation solution inside the target cavity, as a first liposuction stage, to partially dilute the fat and to separate the skin from the muscles and internal organs thereby protecting the adherent lining-tissues from the forceful in and out strokes the surgeon is required to do with the cannulas on the patient's cavity or target zone so that the fat tissue could be more readily torn, crush, tear off, avulsed and, then on, suctioned out as is done in the second sequential stage of the liposuction protocol.

As this technique requires excessive irrigation (infusion of 1.0 to 1.5 cc of irrigation solution for each cc of fat to be removed), it is known as Tumescent Assisted Liposuction (TAL).

While still utilizing the fundamentals of the SAL and TAL protocols, a major technological advance occurred in 1992: the introduction of hollow or solid ultrasonic frequency longitudinally vibrating, or reciprocating, probes inserted via the same small incision through which the surgeon previously makes the infusion of the wetting solution in the target zone. This third current surgical technique is referred to as Ultrasound Assisted Liposuction (UAL).

The ultrasonic frequency vibration apparatus detaches the adipose tissue from its supporting connective scaffold and emulsifies it, i.e. disrupting or fracturing the collagen membrane containing the adipose cells, to convert the adipocyte semi-solid clogging state and texture into an oilier less viscous substance, thereby resulting in more fluid emulsified tissue or material before attempting to suction and dispose it.

The first-generation UAL devices used solid probes, but second-generation devices were characterized by efforts to provide simultaneous suction and emulsification with the very same ultrasonic frequency vibrating cannula. (See e.g. U.S. Pat. No. 4,886,491 to Parisi; U.S. Pat. No. 5,244,458 to Takasu; U.S. Pat. No. 5,419,761 to Narayanan; and U.S. Pat. No. 5,527,273 to Manna). As a result, these first and second generations of UAL devices can be characterized by a solid or hollow round probe with a flat tip, orthogonal to the probe axis, at the distal end of the ultrasonic probe.

In fact, the way the ultrasonic probe emulsifies adipose tissue is by generating acoustic shock waves, caused by the longitudinal or axial displacement of the probe's flat tip, specifically at the distal frontal area perpendicular to the axis of the rod (referred to as the Transverse Emulsification or Fracturing (TEF) area), moving back and forth from 21 up to 60 thousand times per second, i.e. at an ultrasonic frequency. This extremely fast back and forth reciprocation generates shock waves that have a disruptive fracturing effect on the collagenic scaffold of adipocytes, and in general, on any tissue or material present in front of the TEF area.

Although cavitation seems an appropriate term for this phenomenon in water, little if any, cavitation occurs within the viscous texture of the adipose tissue. As a result, cavitation essentially cannot create an emulsification or fracturing effect on fat or any other viscous tissue.

The longitudinal back and forth reciprocation of the ultrasonic solid or hollow probe is originated by a piezoelectric motor connected to the proximal end of the vibrating probe.

This added emulsification stage effect on the tissue being targeted for removal is intended to produce less trauma for the patient and surgeon, as it reduces the traumatic torn, crush, tear off and avulsion of raw non-emulsified tissue that a passive suction cannula imposes on the surrounding structural components, such as for example, skin, vessels, nerves, and connective tissue of the patient. It is also asserted that this emulsification requires less power in the suction pump which means less traumatic torn and avulsion of structural tissues to further protect the patient.

Although a commendable surgical ideal, providing simultaneous suction and emulsification with the very same ultrasonic frequency vibrating cannula proved technically inconvenient, and sometimes quite dangerous for at least the following reasons.

First, because the whole external surface of the long hollow cannula is rubbing against the surrounding structural tissues 24,000 or 36,000 times per second, if these tissues are not completely wet and surrounded by the cooling-wetting solution, the friction generated by the rubbing heats up the tissue, causes instantaneous desiccation, protein coagulation and, consequently, a burn of grave proportions. A patient under anesthesia cannot provide any feedback and the surgeon may inadvertently continue to expand the burn in a rather large area.

Second, given that the suctioning nature of the hollow ultrasonic cannula is to extract fluids, severe burns were caused on the tissue that the very same suction had dried out.

Third, because the emulsification effect of the TEF areas of the ultrasonic probe on the adipocytes is generated perpendicularly to the axis of the cannula, in the frontal surface at the distal end tip of said probe or cannula, the required lumen of the hollow suctioning probe only diminishes the frontal TEF area therefore reducing the efficiency of the desired emulsification.

Fourth, the resulting diminished efficiency of the hollow cannula demanded higher power that only augmented the intrinsic frictional/rubbing risks and complications described in points one and two above.

Fifth, the flat frontal surface of a hollow cannula or solid probe causes an effect known as end hit, whereby the axial acoustic front waves generated at the flat tip have the potential of causing undesired and significant perforations on other organs. A bigger diameter of the frontal area only increases, quadratically, the possibility and size of the end hit deleterious perforations.

Sixth, the efficiency of the emulsification action can only be improved augmenting the frontal cross-sectional area of the probe, but this is not desirable because it augments the size of the accessing incisions on the patient's skin and magnifies the associated risks of burns and perforations.

Hitherto, this contradictive paradox persists as an unsolved technological limitation, and the above-described contradictions characterize what is now known as the first and second generation of UAL devices.

Approximately twenty years ago, an improvement to these first and second generation hollow and solid flat tip ultrasonic devices occurred with the creation of the Vaser® (Vibration Amplification of Sound Energy at Resonance). See e.g. U.S. Pat. No. 6,379,326.

The Vaser® is based on the principle that a hollow ultrasonic cannula with a distal flat TEF area, and its ideally desirable emulsify-while-suctioning effect should be avoided in favor of a "simple" solid probe with a round, bullet shaped distal end or tip at the expense of abandoning the desirable suctioning. The Vaser® solid round tip probe certainly reduced if not eliminated end hit complications and, to replace the perpendicular to the probe's axis, areas required to frontally smash the adipocytes with the acoustic waves, one, two, or three circumferential grooves were machined at the distal end of the probe. See e.g. U.S. Pat. No. 6,368,299.

The use of this grooved device non-suctioning and the resultant protocol are now recognized as tumescent Vaser® Assisted Liposuction, tVAL, and marks the current state of the art for UAL.

The very small emulsification zone, i.e. the grooved 3 mm area located at the distal end of the probe, is an advantage in so-called High Definition surgery as it acts as an sculpting chisel-tip, but in procedures that involve large volume liposuctions it is also a disadvantage or limitation, because it consumes great time and effort, essentially adding a new Vaser® emulsification stage as will be described later.

Despite these design changes, still nowadays, if a surgeon is not well trained or does not provide enough irrigation solution and/or inadvertently touches dry tissue anywhere in the patient's anatomy, the friction burn caused by and along the entirety of the external surface of the solid 330 mm long tVAL probe is instantaneous, unavoidable and leads to lasting consequences to the patient.

Additionally, the current state of the art techniques are characterized by long hours of surgery and anesthesia, typically in the order of four hours and a minimum of two and a half or three hours for a whole body liposuction protocol.

As a result, compression garments, pain drug delivery pumps, and large amounts of anti-inflammatories are required for at least half of the patients, because the procedure, although evolved to be a generally very safe one, is quite traumatic both for the surgeon and for the patient, as will be described below.

Although somewhat innovative, efforts to provide simultaneous irrigation and suction with a concentric dual lumen cannula (see e.g. U.S. Pat. Nos. 5,447,494 and 6,379,326), produced a net (irrigation) minus (suction) zero effect thereby no gain, because the emulsification stage was never incorporated in these devises.

Different efforts to provide "subsonic" frequency motion directly to the suction cannula in a rotating and/or longitudinal manner (see e.g. U.S. Pat. No. 5,112,302), base their relative effectiveness in the macro motion amplitudes to just tear apart and avulse the tissue. This technology, known as PAL, for Power Assisted Liposuction, though is of use in very large liposuction target volumes, is quite traumatic for the surgeon, and of extreme inconvenience in small and delicate areas, such as inner tights, under arms and face.

PAL instruments, rather than emulsifying the tissue to diminish their viscosity and facilitate suction, avulses and tears it apart in a most traumatic manner for other structures such as blood vessels, nerves, lymphatic and connective tissue. In comparison, whereas the macro motion of the subsonic PAL cannula tip/nozzle ranges from 2 to 6 and more millimeters and low frequencies, 100 to 500 displacements per minute, the ultrasonic vibrating probe tip of a UAL device moves 36,000 times per second in fractional displacements or excursions of less than 0.1 mm, which is equivalent, precisely or very close, to the actual size of the adipocyte.

This micro amplitude of the ultrasonic probe-tip frequency warrants that other more cohesive non-adipose neural, lymphatic and vascular structural tissues are kept intact during the process of emulsification. This difference in amplitude is what marks the difference between emulsifying, as proposed herein, versus tearing off and avulsing clogs of adipocytes as found in Power Assisted Liposuction, PAL, subsonic apparatus and, in tSAL protocol.

With tVAL, there are nine basic stages: 1. Insert the irrigation and dissection cannula, 2. Dissect the tissues while infiltrating a biocompatible, wetting or tumescent solution all over the target cavity using numerous back and forth surgeon arm strokes, 3. Remove this infiltration cannula 4. Change instrumentation, and insert the ultrasonic probe, 5. Emulsify the previously infiltrated adipose tissue-cavity by, most commonly, introducing the Vaser® ultrasonic frequency vibratory solid, non-suctioning, probe to fracture and emulsify the adipocytes using hundreds of surgeon back and forth arm strokes (at a rate of about 50-60 per minute), 6. Remove the Vaser® probe, 7. Change instrumentation, insert a different suction cannula, 8. Extract the emulsified solution with the suction cannula connected to a suction pump, using hundreds of back and forth surgeon arm strokes and, finally, 9. Remove this suction cannula and suture the incision.

Stages 1 and 2 are the most traumatic for the patient, as the surgeon needs to access and penetrate the cavity by forcefully and repeatedly inserting, or "stabbing", the patient with a blunt passive cannula. The subsequent tVAL stage does not change or improves this situation at all compared to previous instrumentation and techniques.

The tVAL emulsification stage 5 helps the surgeon by making it easier to extract during stage 8 the fat previously irrigated with wetting solution during stage 2. However, in terms of time and effort, the Vaser®-emulsification yet unproductive no-suction, no-fat extraction adds a new intense labor stage and, consequently, 40 to 50% more time and surgeon traumatic strokes-work to the protocol.

In fact, the emulsification (stage 5) is done for several minutes in each target zone. Given the prevailing tVAL technique, the relatively small 3 mm emulsifying probe tip needs to work out its way all along, around and about the whole 3,000 cc (3,000,000 cubic millimeters) typical liposuction volume throughout the adipose solution without extracting a single cc of tissue.

Quantification of the very intensive work, effort and trauma caused by the surgeon's reciprocating arm repetitive back and forth strokes in and out the patient cavity during a current typical liposuction is particularly significant: a trained surgeon during a typical liposuction, can perform from 60 to 80 back strokes and correspondingly from 60 to 80 forth strokes, i.e. 120 to 160 back and forth strokes with his arm in and out the patients cavity, per minute.

Out of the at least 10,000 average arm strokes in a three hour surgery, 6,000 back and forth strokes per patient performed during Stages 1-6 (irrigation to emulsification) produce ZERO extraction of fat.

Therefore, given the current techniques, in the prevailing state of the art liposuction protocol, 6 out of every 10 in and out strokes of the surgeon are useless as they produce no tangible extraction or measurable outcome; but they do add up to one big inefficient wasted or non-liposuction functional effort that, for both the patient and the surgeon, generates an absurdly traumatic and aggressive type of ineffective work.

Without counting dermatologists, aesthetic surgeons, and other specialties, there are some 43,500 plastic surgeons certified to do the procedure around the world whose liposuction related work is unproductive and wasted 60% of the time.

A skilled surgeon can have one or up to two or three patients per day; this poses great occupational wear and trauma in his shoulder and elbow joints, not to mention fatigue after each of them.

Thus, there is not only a demand for an improved fat removal technique and technology in cosmetic procedures but there is also a great need in the art for a new and improved apparatus to efficiently, effectively, and safely facilitate the removal of hypertrophic fat cells present in the subcutaneous tissue of overweight and obese patients to ameliorate the metabolic syndrome and morbidity related to abdominal obesity.

Also, there is a need to have a multiple channel instrument that once inside the target zone, may perform a diversity of direct confocal/focalized operations and treatments in lieu of a safer, effective and, ideally, 100% efficient surgeon's strokes liposuction.

SUMMARY

One aspect of the disclosure relates to a method for simultaneously emulsifying and removing tissue from a target zone of a patient. The method comprises: creating an incision to access surrounding tissue around the target zone of a patient; inserting an apparatus having integrated irrigation, emulsification and suction through the incision, with the apparatus having an ultrasonic frequency vibrating distal end; activating an irrigation pump coupled to the apparatus, while a suction pump coupled to the apparatus is kept inactive to infuse the surrounding tissue around the target zone with irrigation solution; activating an ultrasonic frequency generator operatively associated with the distal end to vibrate the distal end to dissect the surrounding tissue and provide access to the target zone, with dissection of the surround tissue occurring during infusion of the surrounding tissues; infusing the target zone with the irrigation solution; waiting a period of time until medicament in the irrigation solution has a therapeutic effect on the tissue in the target zone; emulsifying the tissue in the target zone with the activated distal end and extracting the emulsified tissue and the irrigation fluid to dispose the emulsified tissue and irrigation fluid in one single stage, with the apparatus used to both emulsify and extract; continuing the emulsifying and extracting with the apparatus until a desired end point is reached; activating the suction pump to remove any remaining tissue or excess irrigation solution; removing the apparatus from the patient; and closing the incision made on the patient.

The apparatus can be removed from the patient after infusing the target zone and reinserted in the patient prior to emulsifying. The irrigation pump can be activated to compensate for the extracted tissue by providing the irrigation solution in the target zone. In one embodiment, the irrigation and suction pump are activatable to simultaneously extract emulsified tissue and deliver irrigation solution. The ultrasonic frequency generator, which is locatable in a handpiece, can include a piezoelectric motor.

In various embodiments: the apparatus includes a shaft with a proximal end removably coupled to the ultrasonic frequency generator; the apparatus includes a cannula coupled to the handpiece or the shaft; the ultrasonic frequency vibrating distal end is a distal end portion of the shaft; the ultrasonic frequency vibrating distal end is a tip removably attached, integral to, or permanently affixed to a distal end portion of the shaft; a space between a lumen of the cannula and the shaft provides a channel for at least one of irrigation fluid travelling from the irrigation pump and extracted emulsified tissue and irrigation fluid travelling to the suction pump; and/or the cannula is removably coupled to the handpiece and the space provides the channel for the irrigation fluid travelling from the irrigation pump and extracted emulsified tissue and irrigation fluid travelling to the suction pump in an alternating fashion.

In an exemplary embodiment, the apparatus includes an inner cannula coupled to the shaft, with the cannula removably coupled to the handpiece. An annular space between a lumen of the cannula and an outer surface of the inner cannula provides an annular channel for irrigation fluid travelling from the irrigation pump and the space between the lumen of the inner cannula and the shaft provides the channel for extracted emulsified tissue and irrigation fluid travelling to the suction pump.

The apparatus can include an electronic programable control unit for automatically or manually controlling at least one of: volume and flow rate of the irrigation fluid and the extracted emulsified tissue and irrigation fluid; and the ultrasonic frequency generator.

Although the disclosure contemplates that different hard and soft tissues can be used with the apparatus and method disclosed herein, in an exemplary embodiment adipose is the tissue that is emulsified and removed.

As disclosed herein, different configurations of the shaft are envisioned, and in some embodiments, the shaft includes a plurality of fins.

Another aspect of the disclosure relates to an apparatus for removing tissue from a target zone of a patient. The apparatus comprises: a shaft with a distal end and a proximal end, with the proximal end removably attachable to an ultrasonic frequency generator positioned in a cavity of a handpiece; and an outer cannula extending from the handpiece with a distal end and a proximal end, with the proximal end removably attachable to the handpiece and at least a portion of the shaft enclosed by the outer cannula. Activation of the ultrasonic frequency generator transmits vibratory energy through the shaft from the proximal end of the shaft to the distal end of the shaft to emulsify or fracture tissue. A space between a lumen of the outer cannula and the shaft provides a channel for at least one of removing emulsified or fractured tissue from the outer cannula distal end through suction from a suction source and delivering irrigation solution to the outer cannula distal end from an irrigation solution source. The shaft includes a plurality of fins and the distal end of the shaft emulsifies or fractures the tissue.

The apparatus can further comprise an inner cannula extending from the handpiece with a distal end and a proximal end, with the proximal end coupled to the proximal end of the shaft with at least a portion of the inner cannula enclosed by the outer cannula. A space between a lumen of the inner cannula and the shaft provides a suction channel for removing emulsified or fractured tissue from the inner cannula distal end, and the space between the lumen of the outer cannula and an outer surface of the inner cannula provides an irrigation channel for delivering irrigation solution to the outer cannula distal end.

In various embodiments: the inner and outer cannulas are coaxial; the shaft includes protrusions that generate ultrasonic shockwaves to emulsify or fracture tissue; the protrusions are located on the fins of the shaft; the shaft includes three or four fins; the shaft includes three or four fins, with the fins equally spaced from each other; the fins extend from a proximal end portion of the shaft to the distal end of the shaft; the fins extend from a proximal end portion of the shaft, stop at a location along the length of the shaft so that the shaft has a section with no fins, and continue from the section to the distal end of the shaft; the outer cannula includes a portion of reduced diameter, with the portion enclosing the section of the shaft; the portion includes inlet holes; the distal end of the shaft is enclosed by the outer cannula; and/or the distal end of the shaft extends past the outer cannula; the distal end of the shaft is enclosed by the inner cannula.

Another aspect of the disclosure relates to an apparatus for removing tissue from a target zone of a patient, the apparatus comprising: a shaft extending from a handpiece with a distal end and a proximal end, the proximal end removably attachable to an ultrasonic frequency generator positioned in a cavity of the handpiece; and an outer cannula extending from the handpiece with a distal end and a proximal end, the proximal end removably attachable to the handpiece and at least a portion of the shaft enclosed by the outer cannula. Activation of the ultrasonic frequency generator transmits vibratory energy through the shaft from the proximal end of the shaft to the distal end of the shaft to emulsify or fracture tissue. A space between a lumen of the outer cannula and the shaft provides a channel for at least one of removing emulsified or fractured tissue from the outer cannula distal end through suction from a suction source and delivering irrigation solution to the outer cannula distal end from an irrigation solution source. A tip is positioned on the distal end of the shaft, with the tip including a plurality of slits that have an internal surface that generate ultrasonic shockwaves to emulsify or fracture tissue from vibratory motion of the ultrasonic frequency generator with the slits in fluid communication with the channel for suctioning in tissue to be emulsified or fractured and providing an outlet for irrigation solution.

In an exemplary embodiment, the apparatus further comprises an inner cannula extending from the handpiece with a distal end and a proximal end, with the proximal end coupled to the proximal end of the shaft with at least a portion of the inner cannula enclosed by the outer cannula. A space between a lumen of the inner cannula and the shaft provides a suction channel for removing emulsified or fractured tissue from the inner cannula distal end, and the space between the lumen of the outer cannula and an outer surface of the inner cannula provides an irrigation channel for delivering irrigation solution to the outer cannula distal end.

In various embodiments: the inner and outer cannulas are coaxial; the shaft includes three or four fins, with the fins equally spaced from each other; the fins extend from a proximal end portion of the shaft to the distal end of the shaft; the fins extend from a proximal end portion of the shaft, stop at a location along the length of the shaft so that the shaft has a section with no fins, and continue from the section to the distal end of the shaft; the outer cannula includes a portion of reduced diameter, with the portion, which can include inlet holes, enclosing the section of the shaft; the tip is made of metallic, ceramic, polymeric, or composite material; the distal end of the shaft is enclosed by the outer cannula and the tip extends past the outer cannula; and/or the distal end of the shaft is enclosed by the inner cannula and the tip extends past the inner cannula.

Another aspect of the disclosure relates to an apparatus for removing tissue from a target zone of a patient. The apparatus comprises: a shaft extending from a handpiece with a distal end and a proximal end, with the proximal end removably attachable to an ultrasonic frequency generator positioned in a cavity of the handpiece; and an outer cannula extending from the handpiece with a distal end and a proximal end, with the proximal end removably attachable to the handpiece and at least a portion of the shaft enclosed by the outer cannula. Activation of the ultrasonic frequency generator transmits vibratory energy through the shaft from the proximal end of the shaft to the distal end of the shaft to emulsify or fracture tissue. A space between a lumen of the outer cannula and the shaft provides a channel for at least one of removing emulsified or fractured tissue from the outer cannula distal end through suction from a suction source and delivering irrigation solution to the outer cannula distal end from an irrigation solution source. A tip is positioned on the distal end of the shaft, with the tip including a smooth frontal surface area that cannot generate ultrasonic shockwaves and a rear surface area with surface features for generating ultrasonic shockwaves to emulsify or fracture tissue from vibratory motion of the ultrasonic frequency generator. The outer cannula includes slits in fluid communication with the channel for suctioning in tissue to be emulsified or fractured and providing an outlet for irrigation solution.

In one embodiment, the apparatus further comprises an inner cannula extending from the handpiece with a distal end and a proximal end, with the proximal end coupled to the proximal end of the shaft with at least a portion of the inner cannula enclosed by the outer cannula. A space between a lumen of the inner cannula and the shaft provides a suction channel for removing emulsified or fractured tissue from the inner cannula distal end, and the space between the lumen of the outer cannula and an outer surface of the inner cannula provides an irrigation channel for delivering irrigation solution to the outer cannula distal end.

In various embodiments: the inner and outer cannulas are coaxial; the shaft includes three or four fins, with the fins equally spaced from each other; the fins extend from a proximal end portion of the shaft to the distal end of the shaft; the fins extend from a proximal end portion of the shaft, stop at a location along the length of the shaft so that the shaft has a section with no fins, and continue from the section to the distal end of the shaft; the outer cannula includes a portion of reduced diameter, with the portion, which can include inlet holes, enclosing the section of the shaft; the tip is made of metallic, ceramic, polymeric, or composite material; the distal end of the shaft is enclosed by the outer cannula and the tip extends past the outer cannula; and/or the distal end of the shaft is enclosed by the inner cannula and the tip extends past the inner cannula.

Another aspect of the disclosure relates to an apparatus for removing tissue from a target zone of a patient, with the apparatus comprising: a hollow shaft with a distal end and a proximal end, the proximal end removably attachable to an ultrasonic frequency generator positioned in a cavity of a handpiece; and an outer cannula extending from the handpiece with a distal end and a proximal end, the proximal end removably attachable to the handpiece and at least a portion of the shaft enclosed by the outer cannula. Activation of the ultrasonic frequency generator transmits vibratory energy through the shaft from the proximal end of the shaft to the distal end of the shaft to emulsify or fracture tissue. A lumen of the shaft provides a suction channel for removing emulsified or fractured tissue from the shaft distal end through suction from a suction source. A space between a lumen of the outer cannula and an outer surface of the shaft provides an irrigation channel for delivering irrigation solution to the outer cannula distal end from an irrigation solution source. The distal end of the shaft includes a plurality of grooves that emulsifies or fractures the tissue.

In one embodiment, the distal end of the shaft is enclosed by the outer cannula. In another embodiment, the distal end of the shaft extends past the outer cannula.

BRIEF DESCRIPTION OF THE DRAWINGS

A more complete understanding of the present disclosure, and the attendant advantages and features thereof, will be more readily understood by reference to the following description when considered in conjunction with the accompanying drawings wherein:

FIG. 1 shows the currently available state of the art emulsification device, i. e. the Vaser®.

FIG. 2 shows an embodiment of a shaft according to the disclosure with multiple fins for transmitting ultrasonic energy from an ultrasonic generator at a proximal end of the shaft to actuator tip at the distal end of the shaft.

FIG. 3 shows another embodiment of a shaft according to the disclosure with multiple fins for transmitting ultrasonic energy from an ultrasonic generator at a proximal end of the shaft to actuator tip at the distal end of the shaft.

FIG. 4 shows yet another embodiment of a shaft according to the disclosure with multiple fins for transmitting ultrasonic energy from an ultrasonic generator at a proximal end of the shaft to a tip at the distal end of the shaft.

FIG. 8 shows an embodiment of the emulsified tissue removal apparatus according to the disclosure.

FIG. 9A shows another embodiment of the emulsified tissue removal apparatus according to the disclosure.

FIG. 9B shows a cross section through line A-A of FIG. 9A.

DETAILED DESCRIPTION

Figure 5:
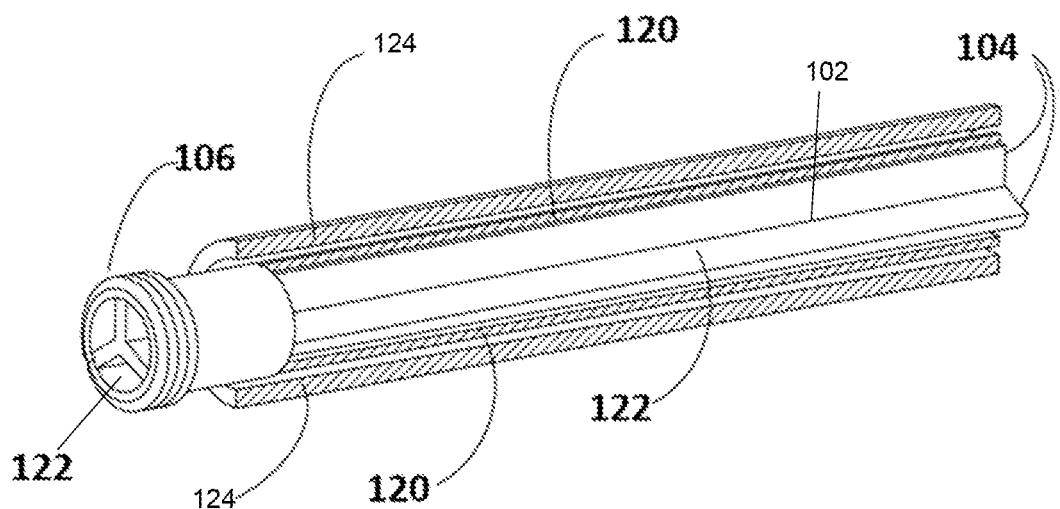
FIG. 5 shows the multiple fins shaft of FIG. 2 incorporated inside a cannula, which in turn is surrounded by an external stationary cannula.

As required, embodiments are disclosed herein; however, it is to be understood that the disclosed embodiments are merely examples and that the methods described below can be embodied in various forms. Therefore, specific structural and functional details disclosed herein are not to be interpreted as limiting, but merely as a representative basis for teaching one skilled in the art to variously employ the present subject matter in virtually any appropriately detailed structure and function. Further, the terms and phrases used herein are not intended to be limiting, but rather, to provide an understandable description of the concepts.

It can be advantageous to set forth definitions of certain words and phrases used throughout this disclosure. The terms "a" or "an", as used herein, are employed to describe elements and components described herein. This is done merely for convenience and to give a general sense of the scope of the disclosure. This description should be read to include one or at least one and the singular also includes the plural unless it is obvious that it is meant otherwise. The term plurality, as used herein, is defined as two or more than two. The term another, as used herein, is defined as at least a second or more.

The term "communicate," as well as derivatives thereof, encompasses both direct and indirect communication. The terms "include" and "comprise," as well as derivatives thereof, mean inclusion without limitation. The term "or" is inclusive, meaning and/or. The phrase "associated with," as well as derivatives thereof, can mean to include, be included within, interconnect with, contain, be contained within, connect to or with, couple to or with, be communicable with, cooperate with, interleave, juxtapose, be proximate to, be bound to or with, have, have a property of, have a relationship to or with, or the like. The phrase "at least one of," when used with a list of items, means that different combinations of one or more of the listed items can be used, and only one item in the list can be needed. For example, "at least one of: A, B, and C" includes any of the following combinations: A, B, C, A and B, A and C, B and C, and A and B and C.

As used herein, the term "about" or "approximately" applies to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure. As used herein, the terms "substantial" and "substantially" means, when comparing various parts to one another, that the parts being compared are equal to or are so close enough in dimension that one skill in the art would consider the same. Substantial and substantially, as used herein, are not limited to a single dimension and specifically include a range of values for those parts being compared. The range of values, both above and below (e.g., "+/−" or greater/lesser or larger/smaller), includes a variance that one skilled in the art would know to be a reasonable tolerance for the parts mentioned.

Note that not all of the activities described above in the general description or the examples are required, that a portion of a specific activity may not be required, and that one or more further activities can be performed in addition to those described. Still further, the order in which activities are listed are not necessarily the order in which they are performed.

In general, the disclosure relates to an apparatus and method that can emulsify or fracture any unwanted tissue as it is being simultaneously suctioned in a synchronous safer and faster manner. Depending on the embodiment, basic characteristics of the device include one or more of the following:

a hollow element that can emulsify and suction at the same time in a synchronous manner,
  an actuator distal end design and geometry (both with and without a tip) to eliminate end hits,
  a tip reciprocating in micro displacement less than 0.1 mm to navigate inside the cavity while protecting tissues (e.g. neural, lymphatic and vascular tissues) other than the target tissue (e.g. adipose),
  a cannula or emulsification probe with a still non-vibrating external surface, to eliminate friction burns and simultaneously infuse irrigation solution or suction unwanted tissue, and
  a small profile so that smaller incisions are required.

These characteristics, as well as others set forth below, result in making most, if not all, surgeon in and out strokes productive (i.e. removing target tissue) compared to the 40% rate for the current techniques, thereby achieving a protocol that is safe, atraumatic, efficient and faster relative to the prior art. Additionally, the wasted energy expended during the multiple in and out ineffective excursions the surgeon made in the previous various separate and unproductive non-suctional stages "against" the patient are obviated entirely. As a result, occupational trauma to the surgeon and iatrogenic injury to the patient are substantially reduced or eliminated almost entirely.

In order to better appreciate the apparatus and method according to the present disclosure, the current state of the art will first be discussed. FIG. 1 is a partial schematic representation of the commercially available Vaser® device 50. Device 50 includes a handpiece 52, which together with protective plastic cone 54, encloses an ultrasonic frequency longitudinal piezoelectric motor 56. A proximal end of an approximately 33 cm long non-insulated solid round vibration probe 58 connects to motor 56 and transmits the vibratory energy to a tip 60 located at the distal end of probe 58. Tip 60 has a bullet shaped distal end to eliminate end hits and can be provided with circumferential grooves 62 to increase the emulsifying effect of tip 60.

The current techniques for the preparation of the tumescent fluid with saline solution, as well as its purposes and doses, are valid for the apparatus and method according to the present disclosure and will not be repeated herein. Also, the configuration and function of the ultrasonic frequency oscillators and generators (as well as the suction pumps or sources and the irrigation fluid pumps or sources), along with their physical engineering parameters, natural resonant frequencies and geometric values, as well as the materials involved in the manufacturing of the vibrating motors, shafts, actuators or cannulas are well known to one of ordinary skill and have been fully disclosed in the patent and technical publications cited herein; therefore, no further discussion is necessary.

Referring to FIG. 2, a partial schematic representation of the new ultrasound frequency vibrating shaft or actuator 100 is shown. As is readily apparent, actuator 100 differs from solid probe 58, as well as the hollow probes that were utilized in other previous devices. Specifically, actuator 100 is provided with one or more fins 102 along its length and TEF areas 104 at its distal end.

Fins 102 provide strength and stability to actuator 100 and, as set forth in more detail below, also serve as conduits for irrigation fluid and emulsified tissue suctioned from the target area. Actuator 100 with fins 102 is more able to withstand ultrasonic reciprocating accelerations while, at the same time, reduces the cross sectional area occupied by the driving shaft thereby providing more space for the suctioned tissue to flow in a most continuous manner and with reduced negative pressure.

Although actuator 100 with fins 102 can be made in any number of suitable ways (e.g. casting, extruding, etc.), exemplary methods of manufacturing are now described. In one method, actuator 100, typically having a length of up to 33 cm, is made by machining fins on a titanium or other material solid round rod all along the axis of the rod. In another method, actuator 100 is made by bending a steel or titanium thin-walled foil to configure fins along the axis of the shaft, and then pressure welding the foils to seal them together.

The number and arrangement of fins 102 can vary depending on the application. In one embodiment, fins 102 are spaced about equal angular (symmetric) angular sectors (for a two fin configuration at 180°; for a three fin configuration at 120°; for a four fin configuration at 90° and so on). The cross section of actuator 102 can have any desired transverse shape such as an "H", "I" or "S" cross sectional beam. In another embodiment, two or more longitudinal fins are constructed parallel to the longitudinal axis of the shaft or slightly inclined in a helix line, like screw threads of very long pitch, even the entire shaft length pitch or longer. In an exemplary embodiment, actuator 100 has a solid structural configuration and fins have a minimum possible transverse, perpendicular to the axis to maximizes the space available to suction the emulsified tissue, thereby increasing the volumetric flow rate.

The geometry of TEF areas 104 generates the shock waves or jackhammer effect, or drilling effect if driven by a rotary motor responsible for emulsifying or fracturing the unwanted tissue in internal chambers, therefore, substantially eliminating any possibility of end hits-perforations to adjacent organs. As shown in FIG. 2, internal TEF areas 104 are flat surfaces that generate an ultrasound stream of shock waves that emulsify the tissue as it is suctioned against it. Alternatively, the transverse surface of internal TEF areas 104 behaves like a mechanical jackhammer that fractures the tissue when suction brings the tissue into contact with TEF areas 104. FIG. 2 shows that each fin 102 has a front surface perpendicular to the longitudinal axis of actuator 100, thereby creating TEF areas 104. Depending on the application, the transverse area of each of fin 102 can be made as wide or as narrow as necessary, reaching micro thin widths for applications in very small or closed zones such as the eye or vascular lumens. Furthermore, the parameters (e.g. materials, geometry, frequency of ultrasonic generator, etc.) can be selected so that the "ultrasonic micro jackhammer" effect is achieved without generating an ultrasonic stream of shock waves.

The proximal end of actuator 100 is provided with a coupler 106 for connection to an ultrasound frequency generator or motor. Although FIG. 2 depicts coupler 106 as threading, the disclosure contemplates any other suitable connection mechanism could be used. FIG. 2 shows one embodiment of the distal end of actuator 100. As described below, the distal end can also be provided with a shaped emulsifying tip, which is either integral to or removable from the distal end of actuator 100. Ultrasonic vibrations are transmitted through actuator 100 to the attached or integral tip Additionally, FIGS. 3 and 4 are partial schematic representations of alternative embodiments of actuators (actuator 108 shown in FIG. 3 and actuator 110 shown in FIG. 4) with additional emulsification elements 112 that increase the surface area and number of TEF areas 104. Elements 112 are knobs, square superimposed elements or other shaped protuberances machined or added to fins 102 to provide additional internal TEF areas 104 along fins 102 at certain locations of the distal end portion of actuator 108, 110. The multiple protuberances/elements 112 on fins 102 provide more ultrasound internal TEF areas 104 and therefore increase the emulsification capacity and consequently the volumetric flow rate of the tissue being extracted.

FIG. 5 is a partial schematic representation of actuator 100 positioned inside an inner cannula 120. Cannula 120 is permanently affixed to actuator 100 or removably secured to actuator 100 and can provide mechanical reinforcement to actuator 100. Additionally, the lumen of cannula 120 together with fins 102 form channels 122 to provide a conduit for irrigation fluid and/or extracted tissue.

The Vaser® solid probe cannot suction the tissues that are being emulsified, at all, therefore adding one more in-out piercing and traumatic strokes stage, increasing the surgical time without extracting a single cc of tissue. As described in more detail below, channels 122 allow simultaneous emulsification and extraction (suction) thereby reducing surgical time and eliminating steps (Stages 4-7) of the current state of the art tVAL protocol.

In use, the assembly of actuator 100 and cannula 120 would be inserted through an outer cannula 124. As opposed to cannula 120, which would transmit the ultrasonic vibrations from the ultrasonic generator or motor, with cannula 124, there is no such transmission. Because outer cannula 124 now remains still and only the distal end portion of actuator 100 and cannula 120 extending from cannula 124 is in contact with the unwanted tissue, the rubbing-friction complications caused by the external surface of the previous vibrating emulsification-suctioning cannulas and emulsifying long vibrating probes are significantly reduced, if not eliminated.

Figure 6:
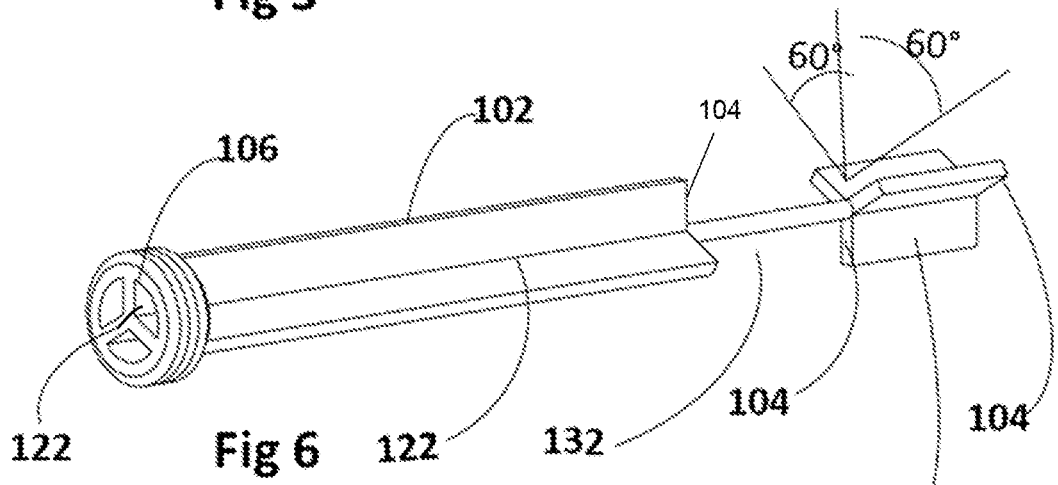
FIG. 6 shows another embodiment of a shaft according to the disclosure with multiple fins for transmitting ultrasonic energy from an ultrasonic generator at a proximal end of the shaft to a tip at the distal end of the shaft.
Figure 7:
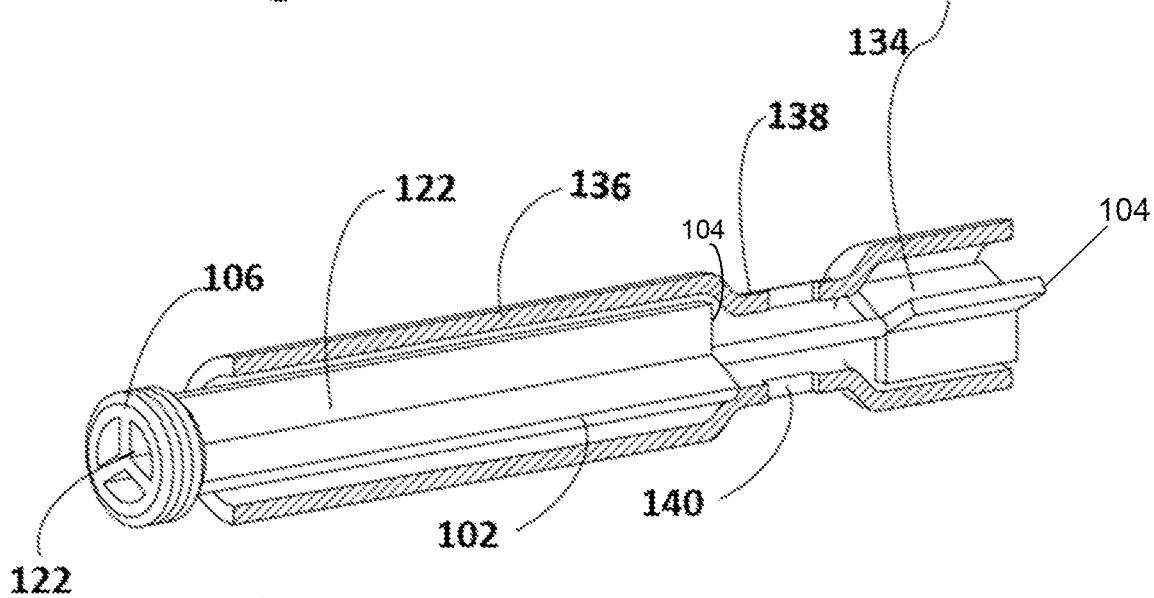
FIG. 7 shows the shaft of FIG. 6 incorporated inside a cannula having a section of reduced diameter to create a drop in pressure resulting in a Venturi effect to induce more tissue volume into the inlet holes.

FIG. 6 is a partial schematic representation of another embodiment of actuator 130. In actuator 130, fins 102 are interrupted by a region 132 without fins 102 and then fins 102 continue at distal end 134. One effect of this structure is to create more TEF areas 104. Another effect of this structure is shown best in FIG. 7 in which actuator 130 is incorporated inside a cannula 136, which is provided with a region 138 of reduced diameter (vena *contracta*) which when suction is applied, creates a pressure drop (Venturi effect) to induce more tissue volume into channels 122 through inlet holes 140.

FIG. 8 is a block diagram illustrating one embodiment of an apparatus 150 according to the disclosure. Apparatus 150 includes actuator 108 positioned inside cannula 124. It should be noted that any of the actuators disclosed herein could be used instead of actuator 108. Actuator 108 is attached to a piezoelectric or any other kind of ultrasound frequency vibrating motor or generator 152 by means of coupler 106. Ultrasonic generator 152 is located within a handpiece 154, which includes a connector 156 for connecting cannula 124. Although connector 156 is shown as threading that mates with threading 158 on cannula 124, any other suitable connection mechanism could be used.

Ultrasonic generator 152 generates longitudinal displacements of actuator 108 coupled to it. The frequency, and accordingly the longitudinal displacement of actuator 108, can be changed to suit the particular application. For adipose tissue, an ultrasonic frequency between about 21 KHz and about 80 KHz is typical, generating an excursion of the distal end of actuator 108 of about 40 to about 120 microns.

The distal end of actuator 108 has internal TEF areas 104 perpendicular to the longitudinal axis of actuator 108. The movement of these internal TEF areas 104 generate the ultrasound shockwave stream that emulsifies the incoming tissue suctioned into cannula 124. Internal TEF areas 104 may be positioned slightly inside or outside cannula 124 depending on what results or purpose the surgeon needs in terms of penetrating fibrous tissues, disposing large volumes of unwanted tissue, or fracturing and suctioning hard tissues. The number and location of additional internal emulsification elements 112 can be selected to have the desired tissue emulsification and thereby the volumetric flow rate of tissue disposed.

Also, in an embodiment similar to that of FIG. 8 but on a smaller scale, exposing the distal end of the actuator slightly (e.g. a millimeter or less) out of the external cannula is of use during the extraction of harder tissues in certain surgical protocols, such as phacoemulsification in ophthalmology, atherectomy in vascular, and lithiasis in urology. This configuration eliminates the conflict that happens in the previous techniques whereby the ultrasound shock wave generated at the distal end of the probe rejects the tissue that the surgeon wants to suction and dispose.

In general, when trying to fracture and suction hard tissues or materials this conflict is critical, and chronic, with all the previous phacoemulsification technologies, as their flat external frontal TEF surface pushes away the tissue supposed to be pulled in. On the contrary, with the disclosed apparatus and method, the tissue suctioned into the suction cannula is emulsified or fractured via jackhammer effect when the tissue touches or is already inside the apparatus eliminating the ultrasonic stream push away vs the suction pulling conflict.

Because the emulsified or fractured tissue has a lower viscosity, rather than conflicting each other, now, one effect, fracturing-emulsification, enhances the other, suction fluidity, and vice versa, suction causes emulsification, in a synchronous self-induced manner.

Given the ad hoc unification of the separate irrigation, emulsification, and suction devices into one handpiece and apparatus with the synchronous effectiveness, much less effort is demanded, less surgical time is required, and less trauma is caused.

As shown in FIG. 8, a manifold 160 is used to couple an irrigation source or pump 162 and a suction source or pump 164 to cannula 124 and irrigation and suction pumps 162, 164 can be activated alternately as needed during the procedure. The disclosure envisions connection mechanisms other than manifold 160. The connection to both a suction and an irrigation pump is used to compensate, in real time and a controlled continuous or pulsed manner, the rapid loss of wetting solution within the patient's target zone, as needed to prevent complications in a dried-out cavity. In this regard, irrigation and suction volume meters can be used to measure and compare, in real time, the irrigation and suction volumes of fluids being respectively infused in and sucked out of the patient's cavity. Further, the apparatus and method according to the disclosure can keep real time feedback control over the irrigation and suction volumes to proportionally and as needed equilibrate them to avoid sudden vacuum or cavity collapse or clogging, and to keep the procedure tumescent, controlled and safe.

Apparatus 150 can be used for the synchronic suction and emulsification of either soft adipose tissue, or hard tissues such as cataracts in ophthalmology, kidney stones in urology, or clog removal in vascular applications. Depending on whether suction pump 164 or irrigation pump 162 is activated, channels 122 (formed by the lumen of cannula 124 and fins 102) alternately serve as suction and irrigation conduits.

Thus, the disclosure provides a method by which fat or any other type of tissue or material is suctioned into the cannula and is made to flow along the multiple fins shaft attached to the ultrasonic generator since the activation of the suction pump and the vibrating actuator inside the surrounding cannula suctions, emulsifies and extracts the targeted tissue simultaneously in one single stage and in a synchronous optimized manner.

FIGS. 9A and 9B show another embodiment of an apparatus 170 according to the disclosure. Actuator 100 with cannula 120 affixed or secured thereto is attached to ultrasonic generator 152 and inserted inside outer cannula 124 which is attached to handpiece 154. It should be noted that any of the actuators disclosed herein could be used instead of actuator 100. The use of two cannulas provides a separate conduit (i.e. the space between the lumen of cannula 124 and external wall of cannula 120) for irrigation fluid and a separate conduit (i.e. channel 122 created by fins 102 and the lumen of cannula 120) for suction. As a result, irrigation solution from irrigation pump 162 attached to cannula 124 can be provided in a continuous manner, while suctioning of the unwanted tissue is simultaneously being performed using suction pump 164 connected to the proximal end of the cannula 120. Simultaneous emulsification is done with TEF areas 104 located at the distal end of actuator 100. This configuration is particularly useful in certain instances when simultaneous irrigation, suction and emulsification is needed in applications such as, for example, cataracts removal in ophthalmology.

The integration of an irrigation channel with the now safe and functional emulsification and suction apparatus is desirable to generate a real time supply of wetting solution during the liposuction stage to compensate the accelerated extraction of unwanted tissue. FIGS. 8 and 9A and 9B illustration two ways of achieving this: one, integrating a thin-walled cannula to the apparatus or, two, alternating the suction and irrigation pumps actions during surgery using a stationary external cannula connected to the handpiece.

Figure 10:
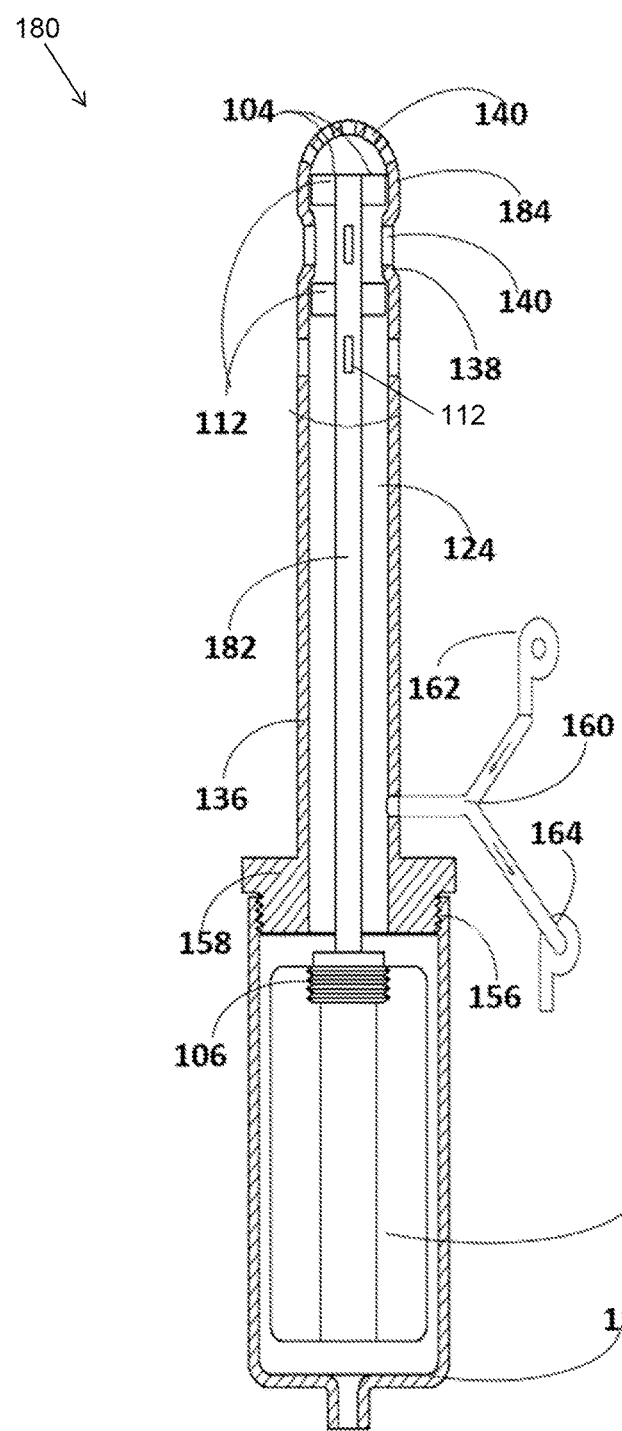
FIG. 10 shows another embodiment of the emulsified tissue removal apparatus according to the disclosure.

FIG. 10 is a block diagram illustrating another embodiment of an apparatus 180 according to the disclosure. Apparatus 180 includes an actuator 182 positioned inside cannula 136. Unlike the previously disclosed actuators, actuators 182 does not have fins and instead is a solid or hollow rod with a distal end including TEF areas 104 and additional emulsifying elements 112 located on the distal end portion. Actuator 182 is attached to a piezoelectric or any other kind of ultrasound frequency vibrating motor or generator 152 by means of coupler 106. Ultrasonic generator 152 is located within a handpiece 154, which includes a connector 156 for connecting cannula 136. Although connector 156 is shown as threading that mates with threading 158 on cannula 136, any other suitable connection mechanism could be used.

Cannula 136 can be provided with a protective end covering 184 which, like region 138, includes inlet holes 140. The geometry of covering 184 can be selected depending on the application. Typically, a bullet shape end can be used. Irrigation pump 162 and suction pump 164 are attached to cannula 136 via manifold 160 and used alternately as needed.

Figure 11:
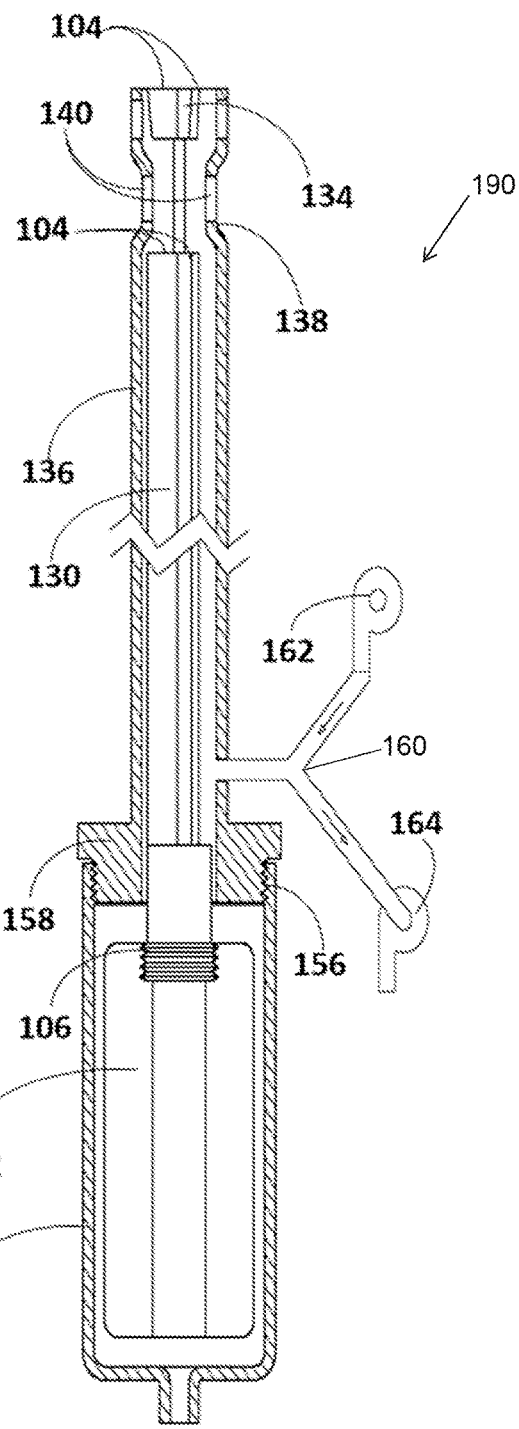
FIG. 11 shows another embodiment of the emulsified tissue removal apparatus according to the disclosure.

FIG. 11 is a block diagram illustrating another embodiment of an apparatus 190 according to the disclosure. Apparatus 190 includes actuator 130 positioned inside cannula 136. Actuator 130 is attached to a piezoelectric or any other kind of ultrasound frequency vibrating motor or generator 152 by means of coupler 106. Ultrasonic generator 152 is located within a handpiece 154, which includes a connector 156 for connecting cannula 136. Although connector 156 is shown as threading that mates with threading 158 on cannula 136, any other suitable connection mechanism could be used. As previously described with references to FIGS. 6 and 7, actuator 130 has internal TEF areas 104 and fins 102 are interrupted by a region 132 without fins 102 and then fins 102 continue at distal end 134. As also previously described, cannula 136 is provided with a region 138 of reduced diameter (vena *contracta*) which when suction is applied, creates a pressure drop (Venturi effect) to induce more tissue volume into channels 122 through inlet holes 140. Irrigation pump 162 and suction pump 164 are attached to cannula 136 via manifold 160 and used alternately as needed.

Figure 12:
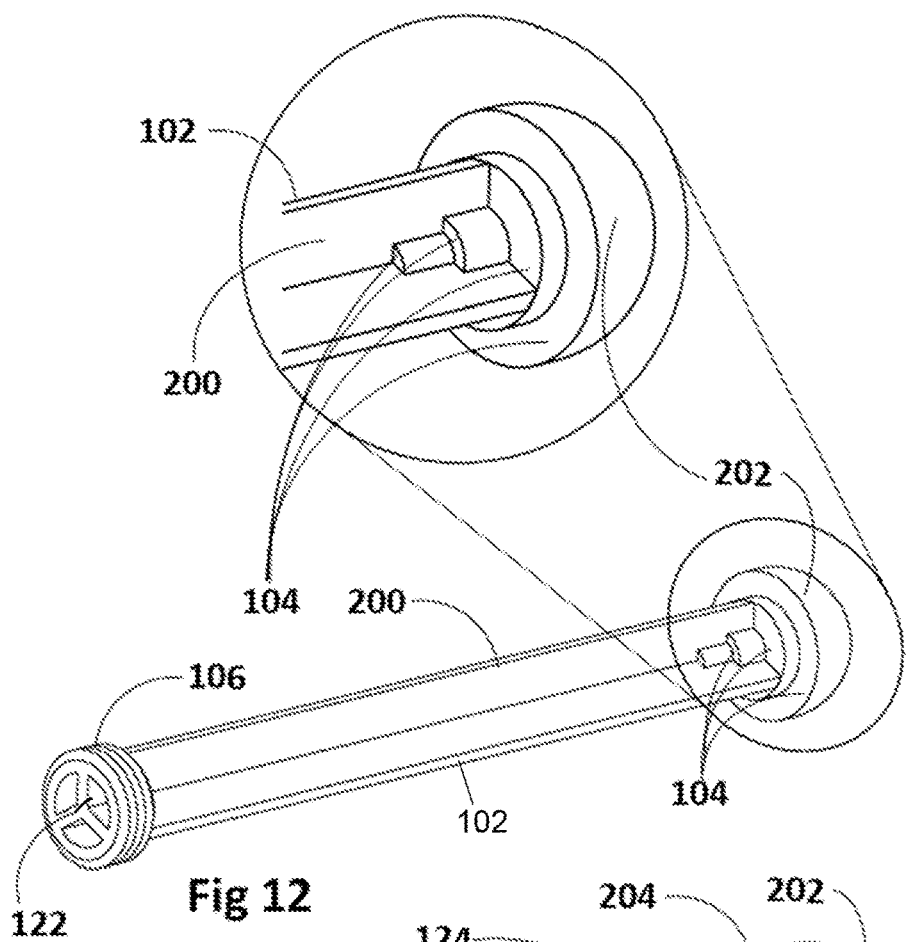
FIG. 12 shows an embodiment of a shaft according to the disclosure with multiple fins for transmitting ultrasonic energy from an ultrasonic generator at a proximal end of the shaft to a retrograde emulsifying tip at the distal end of the shaft.

Although the above description focusses on actuators with TEF areas 104 (with or without additional emulsifying elements 112) that correspond to the general geometry of the actuators, any of the above disclosed actuators can be provided with a specially shaped tip (either integral to or removable from the actuator). In this regard, FIG. 12 is a partial schematic representation of an actuator 200 with a retrograde emulsification tip 202 removably attached. Actuator 200 is provided with one or more fins 102 along its length and a generally hemispherical tip 202 includes internal TEF areas 104 located at its rear end so that the circular stream of ultrasonic shock waves is projected backwards thereby protecting the patient from possible end hits. The proximal end of actuator 200 is provided with a coupler 106 for connection to an ultrasound frequency generator or motor.

Figure 13:
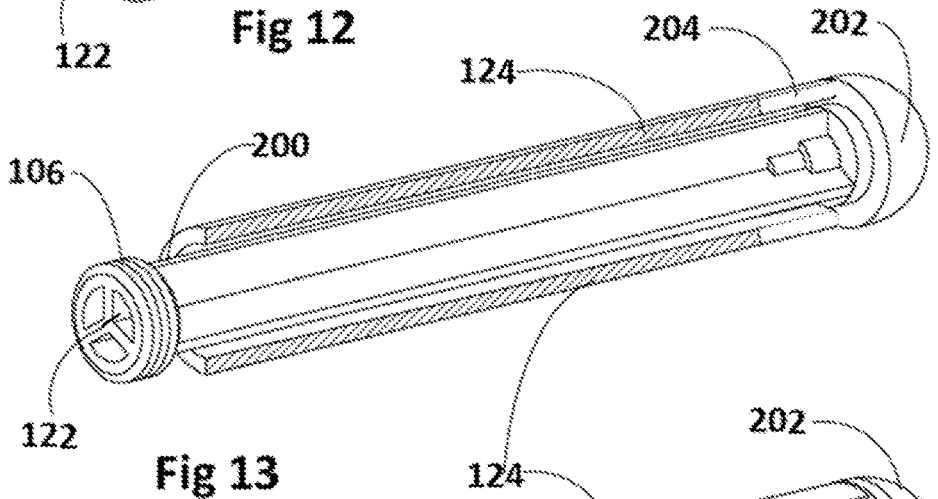
FIG. 13 shows the shaft of FIG. 12 placed inside a cannula.
Figure 14:
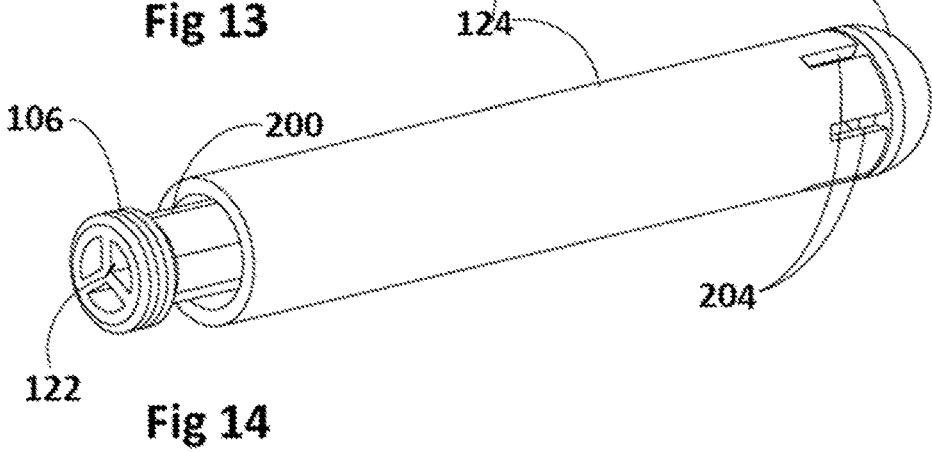
FIG. 14 shows the shaft/cannula assembly of FIG. 13 inserted in a stationary external cannula having inlet slots.
Figure 15:
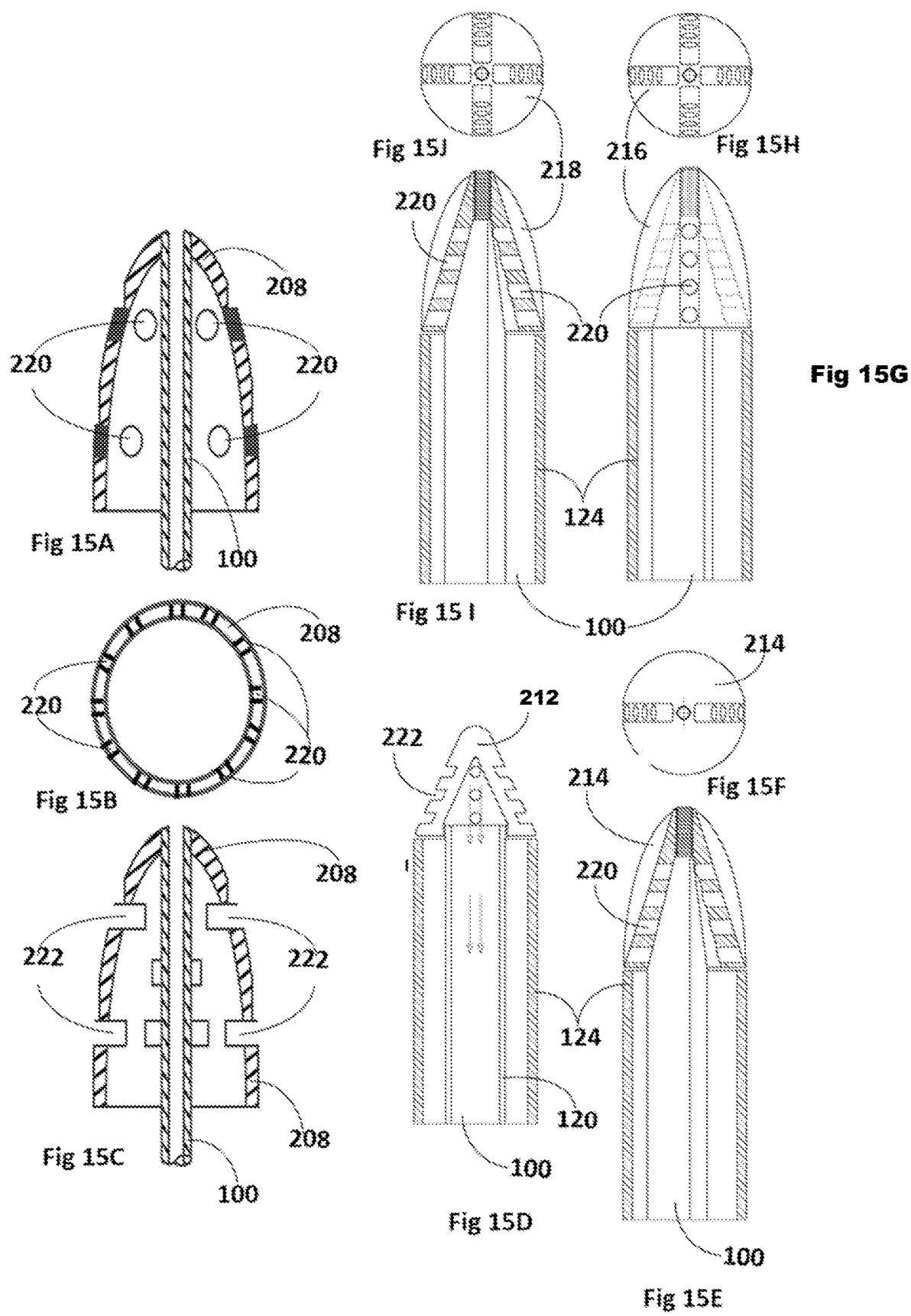
FIGS. 15A-J show multiple possible configurations of the distal end tips with internal holes or slots that serve as peripheral emulsification chambers.

FIG. 13 is a partial schematic representation of actuator 200 positioned inside cannula 124 so that the tissue emulsified by retrograde emulsification surfaces 104 can be disposed using a suction pump connected to cannula 124. In this regard, FIG. 14 shows cannula 124 is provided with multiple inlet slots 204 through which the tissue can be suctioned and directed towards internal retrograde TEF areas 104 and disposed through cannula 124.

FIGS. 15A-J show different embodiments of tips 208, 210, 212, 214, 216, 218 usable with any of the actuators disclosed herein. Tips 208, 210, 212, 214, 216, 218 can be bullet shaped, conical, or have any other suitable shape and can be made of titanium, stainless steel, aluminum, or any other suitable material such as other metals, ceramic, or composites. Tips 208, 210, 212, 214, 216, 218 are provided with internal holes or slots 222 that serve as peripheral emulsification chambers 220. Tips 208, 210, 212, 214, 216, 218 can be either integral with, permanently affixed to, or removably attached to any of the actuators disclosed herein. For removable tips, an attaching hole, threaded or other method, can be used to connect the tip to the actuator. Internal emulsification chambers 220 emulsify the tissue as it is suctioned through cannula 120, 124, so that the stream of ultrasonic shock waves is projected inwards thereby protecting the patient from possible end hits.

The integrated or separated tip is sculpted, or machined, with vertical holes or slots with surfaces orthogonal to the actuator and cannula axes. These internal fracturing surfaces make for the peripheral TEF area that the tissue emulsification or fracturing need, yet functioning as internal, or hidden, emulsification chambers. Therefore, end hit complications caused by the flat distal end of previous vibrating emulsification-suctioning cannulas and emulsifying long vibrating probes are reduced, if not eliminated. Also, the efficiency of the emulsification process is increased by the suction pressure that forces the tissue into the TEF areas and the emulsified tissue then increases the efficiency and speed of the suctioned tissue in a synchronic manner.

Because one hole or slot on the integrated or separated tip can by itself make for the total frontal or TEF area found in prior UAL devices, the separated or floating suction cannula tips disclosed herein can significantly increase the frontal TEF area by simply providing as many holes or slots as necessary on its circumference and in accordance to the hard or soft tissue objective of the surgery.

Because in apparatus disclosed herein the TEF area in the actuator is not restricted to the diameter of a solid fixed geometry internal actuator that blocks the internal available lumen, smaller Outside Diameter (OD) cannulas may be fabricated without losing and even increasing the Volumetric Flow Rate (VFR) of the suctioned tissue.

Because the cross-sectional area of the tip actuator inside a suction cannula is a quadratic function of its diameter, the possible VFR of tissue extracted decreases quadratically as the actuator diameter is increased to withstand the high accelerations to which it is subject by the ultrasonic generators. On the other hand, slender or solid actuators of small diameters designed to increase the internal lumen and thereby the possible VFR of tissue extracted motor may cause erratic and uncontrollable behaviors given certain resonant parameters generated at the ultrasound frequency vibrating motor.

This said, one aspect of the disclosure relates to an ultrasonic vibrating multiple fins shaft-actuator structure to replace the slender solid shafts, and to activate any of the integrated or separated tips that emulsify or fracture the tissue.

Figures 16, 17:
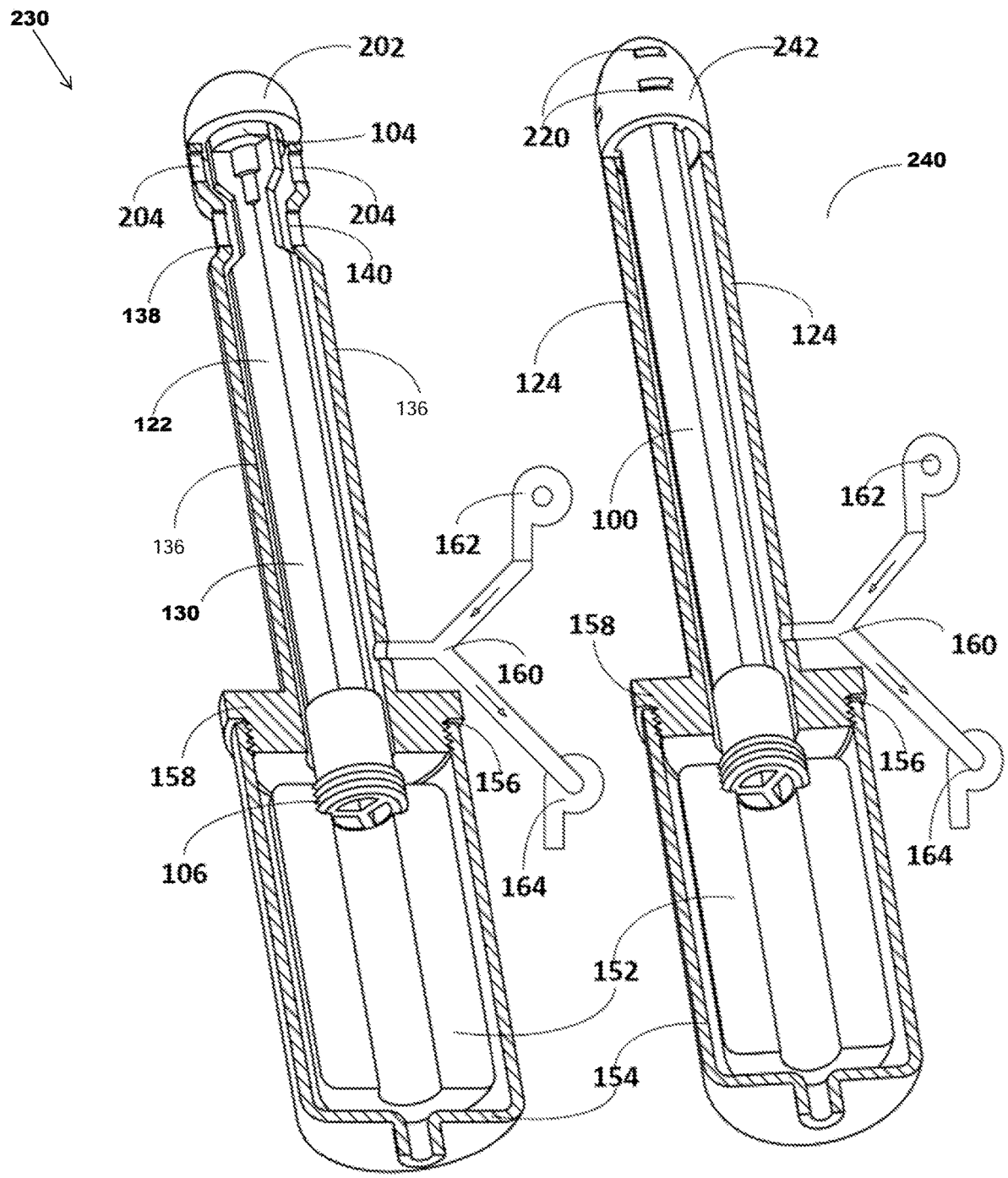
FIG. 16 shows another embodiment of the tissue removal apparatus according to the disclosure which includes a shaft with multiple fins for transmitting ultrasonic energy from an ultrasonic generator at a proximal end of the shaft to a retrograde emulsifying tip at the distal end of the shaft.
FIG. 17 shows another embodiment of the tissue removal apparatus according to the disclosure which includes a shaft with multiple fins for transmitting ultrasonic energy from an ultrasonic generator at a proximal end of the shaft to an internal emulsification chamber tip at the distal end of the shaft.

FIG. 16 is a block diagram illustrating another embodiment of an apparatus 230 according to the disclosure. Apparatus 230 includes actuator 130 with retrograde emulsification tip 202 affixed/attached thereto. Actuator 130 is positioned inside cannula 136. Actuator 130 is attached to a piezoelectric or any other kind of ultrasound frequency vibrating motor or generator 152 by means of coupler 106. Ultrasonic generator 152 is located within a handpiece 154, which includes a connector 156 for connecting cannula 136. Although connector 156 is shown as threading that mates with threading 158 on cannula 136, any other suitable connection mechanism could be used.

As also previously described, cannula 136 is provided with a region 138 of reduced diameter (vena *contracta*) which when suction is applied, creates a pressure drop (Venturi effect) to induce more tissue volume into channels 122 through inlet holes 140. Irrigation pump 162 and suction pump 164 are attached to cannula 136 via manifold 160 and used alternately as needed. It is noted that the emulsification done inside retrograde emulsification surfaces 104 is induced by the simultaneous suctioning of the tissue through cannula 136, and this emulsified tissue is what, in a synchronic effect increases the fluidity of the tissue being disposed at increased volumetric flow rate through cannula 136.

FIG. 17 is a block diagram illustrating another embodiment of an apparatus 240 according to the disclosure. Apparatus 240 includes actuator 100 with tip 242 affixed/attached thereto. Tip 242 includes internal emulsifying chambers 220. Actuator 100 is positioned inside cannula 124. Actuator 100 is attached to a piezoelectric or any other kind of ultrasound frequency vibrating motor or generator 152 by means of coupler 106. Ultrasonic generator 152 is located within a handpiece 154, which includes a connector 156 for connecting cannula 124. Although connector 156 is shown as threading that mates with threading 158 on cannula 124, any other suitable connection mechanism could be used. Irrigation pump 162 and suction pump 164 are attached to cannula 124 via manifold 160 and used alternately as needed. It is noted that the emulsification done inside the emulsification chambers 220 is induced by the simultaneous suctioning of the tissue, and this emulsified tissue coming in through the emulsification chambers 220 is what, in a synchronic effect, increases the fluidity of the tissue being disposed at increased volumetric flow rates through cannula 124.

Figure 18:
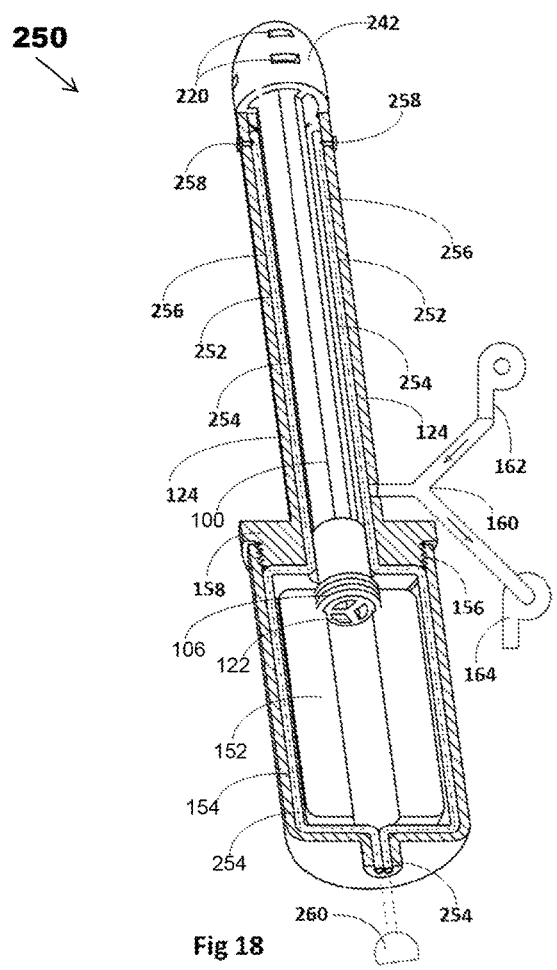
FIG. 18 is another embodiment of the tissue removal apparatus according to the disclosure.

FIG. 18 is a block diagram illustrating another embodiment of an apparatus 250 according to the disclosure. Apparatus 250 includes actuator 100 with tip 242 affixed/attached thereto. Tip 242 includes internal emulsifying chambers 220. Actuator 100 is positioned inside cannula 124. Actuator 100 is attached to a piezoelectric or any other kind of ultrasound frequency vibrating motor or generator 152 by means of coupler 106. Ultrasonic generator 152 is located within a handpiece 154, which includes a connector 156 for connecting cannula 124. Although connector 156 is shown as threading that mates with threading 158 on cannula 124, any other suitable connection mechanism could be used. Irrigation pump 162 and suction pump 164 are attached to cannula 124 via manifold 160 and used alternately as needed.

As shown in FIG. 18, wall 252 of cannula 124 includes one or more insulated channels 254 that may carry cables 256 connecting treatment electrodes or sensors 258 located at the distal end of cannula 124 with the energy supply and control circuitry of the CPU or PLC 260. Electrodes or sensors 258 can be used to achieve other surgical objectives, such as for example coagulation or cauterization, or aesthetic results such for example skin tightening, neocollagenesis etc., directly to the internal side, epidermis, of the skin.

CPU or PLC 260 (or any other suitable controller) can be used along with the associated power supplies and electronic circuitry to manage the different suction and irrigation pumps, the ultrasound frequency oscillator and any other kind of sensors or actuators so as to allow programable, automatic or manual control of a simultaneous, alternate, pulsed or continuous application of any of the apparatuses disclosed herein. In this regard, CPU or PLC 260 can provide automatic, programable, or manual control of a simultaneous, alternate, pulsed or continuous application of any one of the apparatus disclosed herein.

Figure 19:
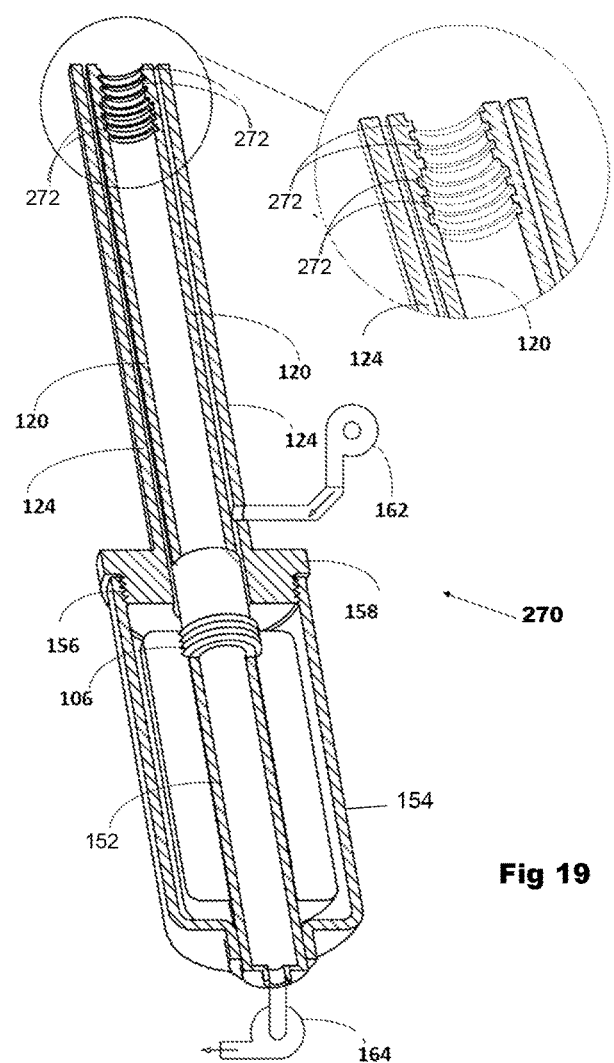
FIG. 19 is another embodiment of the tissue removal apparatus according to the disclosure.
Figure 20:
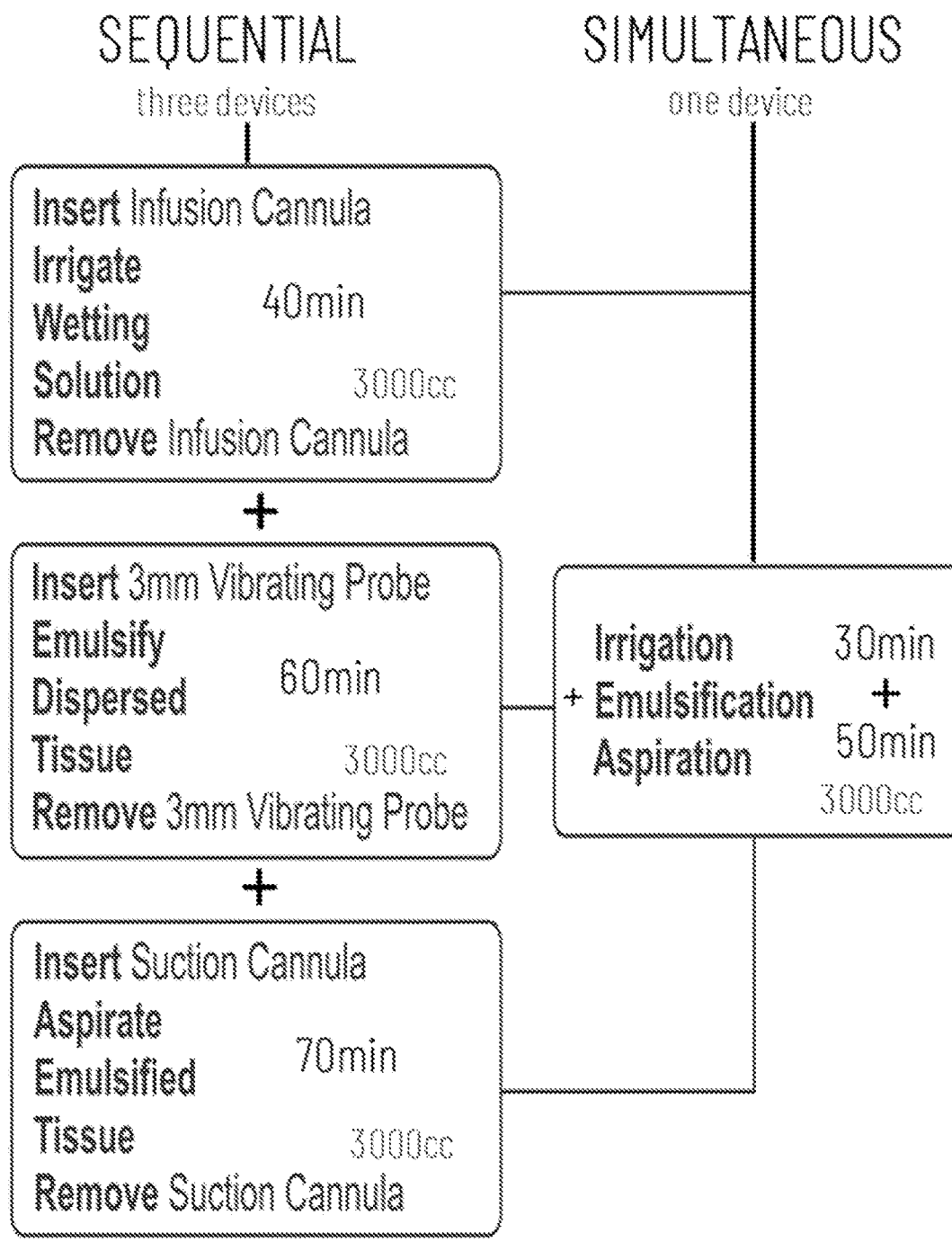
FIG. 20 compares the disclosed apparatus and method to the prior art.

FIG. 19 is a block diagram illustrating another embodiment of an apparatus 270 according to the disclosure. There are two ways to view apparatus 270. First, apparatus 270 can be viewed as having inner and outer cannulas and no shaft or actuator, with the inner cannula provided with TEF areas. Second, apparatus 270 can be viewed has having an actuator or shaft that is a hollow rod and an outer cannula. Although the following description of apparatus 270 takes the first view, the second view is equally applicable.

Apparatus 270 includes inner cannula 120 with grooves or veins 272 (which can be machined, etched, or otherwise formed) on the distal end of its inner surface. Grooves 272 function as the TEF areas. The number and configuration of grooves 272 can be chosen depending on the clinical application Inner cannula 120 is attached to a piezoelectric or any other kind of ultrasound frequency vibrating motor or generator 152 by means of coupler 106. Ultrasonic generator 152 is located within handpiece 154. Inner cannula 120 is surrounded by outer cannula 124 which is attached to the handpiece 154 by means of coupler 156. Although connector 156 is shown as threading that mates with threading 158 on cannula 124, any other suitable connection mechanism could be used. Irrigation pump 162 is attached to cannula 124, and the suction pump is attached to the proximal end of cannula 120.

It is noted that the emulsification done inside cannula 120 is induced by grooves 272. The tissue forcedly suctioned into cannula 120 contacting grooves 272 is what, in a synchronic effect, increases the fluidity of the tissue being disposed, thereon, at increased volumetric flow rates through cannula 120 without disrupting the surrounding structural tissue.

Having detailed the apparatus according to the disclosure, typical methods according to the disclosure of using the various apparatuses for emulsifying tissue will now be described. In general, the methods according to the disclosure relate to removing adipose or any other unwanted soft or had tissue from a patient. As a particular example, in the field of liposuction, the protocol starts by first creating an incision in the skin of a patient. Depending on the clinical application one of the apparatuses (150, 170, 180, 190, 230, 240, 250, 270) is inserted through the incision and into the target zone of the patient.

Irrigation pump 162 and ultrasonic generator 152 are activated to: A. convey and force tumescent solution into the target zone; B. simultaneously/synchronically dissect tissue in one single stage; C. provide visual and tactile feedback on the tumescent cavity. The activation of ultrasonic generator 152 transmits the ultrasonic vibratory energy to the actuator (100, 108, 110, 130, 182, 200) used with the apparatus. The surgeon waits a sufficient time (e.g. about 15 minutes) to allow the irrigation solution to have is anesthetic (typically from lidocaine) and vasoconstrictive (typically from epinephrine) effects.

This Ultrasound Assisted Irrigation UAI technique significantly alleviates the trauma associated with stabbing of the patient with a blunt passive cannula and has never before been used in this stage of the liposuction protocol. The UAI stage is done with the apparatuses as disclosed herein. In this manner, the initial and most traumatic stages (stages 1 and 2 described above) of the liposuction protocol, the irrigation or infiltration of the tumescent solution and the initial "penetration" of the cavity with a blunt passive cannula, are now facilitated by the disclosed apparatus and method.

Although the disclosure contemplates that the surgeon can use any of the apparatus as disclosed herein, in an exemplary embodiment, the same apparatus used for the combined irrigation and dissection is then inserted through the same incision and into the target zone and suction pump 164 is activated while simultaneously activating the actuator to: D. convey the adipose tissue emulsion directly towards the emulsification multiple fins shaft of the actuator; E. simultaneously/synchronically extract the now rapidly emulsified or fractured tissue, to dispose it in one single stage; and F. have visual feedback on the results. In some embodiments, irrigation pump can also be activated to have simultaneous/synchronous irrigation, emulsification, and suction (removal) of tissue.

After the desired amount of tissue is removed, the apparatus is removed from the patient and the incision is closed.

FIG. 19 is a schematic illustration comparing the disclosed apparatus and method to the prior art. The nine stages of the current state-of-the-art liposuction procedure typically requires at least 170 minutes for an average 3,000 cc volume of extracted tissue emulsion. In contrast, simultaneous suction-emulsification-irrigation stages integrated in the apparatus and method according to the disclosure devise reduce the total time to about 80 minutes estimated for the average 3,000 cc volume of extracted tissue emulsion.

All references cited herein are expressly incorporated by reference in their entirety. It will be appreciated by persons skilled in the art that the present disclosure is not limited to what has been particularly shown and described herein above. In addition, unless mention was made above to the contrary, it should be noted that all of the accompanying drawings are not to scale. There are many different features to the present disclosure and it is contemplated that these features may be used together or separately. Thus, the disclosure should not be limited to any particular combination of features or to a particular application of the disclosure. Further, it should be understood that variations and modifications within the spirit and scope of the disclosure might occur to those skilled in the art to which the disclosure pertains. Accordingly, all expedient modifications readily attainable by one versed in the art from the disclosure set forth herein that are within the scope and spirit of the present disclosure are to be included as further embodiments of the present disclosure.

The description in the present application should not be read as implying that any particular element, step, or function is an essential or critical element that must be included in the claim scope. The scope of patented subject matter is defined only by the allowed claims. Moreover, none of the claims invokes 35 U.S.C. § 112(f) with respect to any of the appended claims or claim elements unless the exact words "means for" or "step for" are explicitly used in the particular claim, followed by a participle phrase identifying a function.

Benefits, other advantages, and solutions to problems have been described above with regard to specific embodiments. However, the benefits, advantages, solutions to problems, and any feature(s) that can cause any benefit, advantage, or solution to occur or become more pronounced are not to be construed as a critical, required, sacrosanct or an essential feature of any or all the claims.

After reading the disclosure, skilled artisans will appreciate that certain features are, for clarity, described herein in the context of separate embodiments, can also be provided in combination in a single embodiment. Conversely, various features that are, for brevity, described in the context of a single embodiment, can also be provided separately or in any sub-combination. Further, references to values stated in ranges include each and every value within that range.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

What is claimed is:

1. A method for simultaneously emulsifying and removing tissue from a target zone of a patient, the method comprising:
    creating an incision to access surrounding tissue around the target zone of a patient;
    inserting an apparatus having integrated irrigation, emulsification and suction through the incision, the apparatus having an ultrasonic frequency vibrating distal end;
    activating an irrigation pump coupled to the apparatus, while a suction pump coupled to the apparatus is kept inactive to infuse the surrounding tissue around the target zone with irrigation solution;
    activating an ultrasonic frequency generator operatively associated with the distal end to vibrate the distal end to dissect the surrounding tissue and provide access to the target zone, with dissection of the surround tissue occurring during infusion of the surrounding tissues;
    infusing the target zone with the irrigation solution;
    waiting a period of time until medicament in the irrigation solution has a therapeutic effect on the tissue in the target zone;
    emulsifying the tissue in the target zone with the activated distal end and extracting the emulsified tissue and the irrigation fluid to dispose the emulsified tissue and irrigation fluid in one single stage, with the apparatus used to both emulsify and extract;
    continuing the emulsifying and extracting with the apparatus until a desired end point is reached;
    activating the suction pump to remove any remaining tissue or excess irrigation solution;
    removing the apparatus from the patient; and
    closing the incision made on the patient,
    wherein the apparatus includes a shaft with proximal and distal end portions and formed by a plurality of longitudinal fins extending continuously from the proximal end portion to the distal end portion to transmit vibrations to the distal end of the apparatus and wherein each of the plurality of longitudinal fins has a height that extends from a center of the shaft to a periphery of the shaft.

2. The method of claim 1, wherein the irrigation and suction pump are activatable to simultaneously extract emulsified tissue and deliver irrigation solution.

3. The method of claim 2, wherein the ultrasonic frequency generator includes a piezoelectric motor.

4. The method of claim 3, wherein the ultrasonic frequency generator is located in a handpiece.

5. The method of claim 4, wherein the proximal end portion of the shaft is removably coupled to the ultrasonic frequency generator.

6. The method of claim 5, wherein the apparatus includes a cannula coupled to the handpiece without coupling to the ultrasonic frequency generator.

7. The method of claim 6, wherein the ultrasonic frequency vibrating distal end is the distal end portion of the shaft.

8. The method of claim 6, wherein the ultrasonic frequency vibrating distal end is a tip removably attached, integral to, or permanently affixed to the distal end portion of the shaft.

9. The method of claim 8, wherein a space between a lumen of the cannula and the plurality of longitudinal fins of the shaft provides a channel for at least one of irrigation fluid travelling from the irrigation pump and extracted emulsified tissue and irrigation fluid travelling to the suction pump.

10. The method of claim 9, wherein the space provides the channel for the irrigation fluid travelling from the irrigation pump and extracted emulsified tissue and irrigation fluid travelling to the suction pump in an alternating fashion.

11. The method of claim 9, wherein the apparatus includes an electronic programmable control unit for automatically or manually controlling at least one of: volume and flow rate of the irrigation fluid and the extracted emulsified tissue and irrigation fluid; and the ultrasonic frequency generator.

12. The method of claim 1, wherein the emulsified and removed tissue is adipose.

13. The method of claim 1, wherein each of the plurality of longitudinal fins is equally spaced from each other.

14. An apparatus for removing tissue from a target zone of a patient, the apparatus comprising:
    a shaft extending from a handpiece with a distal end and a proximal end, the proximal end removably attachable to an ultrasonic frequency generator positioned in a cavity of the handpiece and the shaft formed by a plurality of substantially straight longitudinal fins extending continuously from the proximal end portion of the shaft to the distal end of the shaft; and
    a cannula extending from the handpiece with a distal end and a proximal end, the proximal end removably attachable to the handpiece and at least a portion of the shaft enclosed by the cannula,
    wherein activation of the ultrasonic frequency generator transmits vibratory energy through the shaft from the proximal end of the shaft to the distal end of the shaft to emulsify or fracture tissue,
    wherein a space between a lumen of the outer cannula and the plurality of longitudinal fins of the shaft provides a channel for at least one of removing emulsified or fractured tissue through suction from a suction source and delivering irrigation solution to the outer cannula distal end from an irrigation solution source,
    wherein a bullet-shaped tip is positioned on the distal end of the shaft, the tip including a smooth frontal cylindrical surface area that cannot generate ultrasonic shockwaves and a plurality of perforations with rear flat surfaces perpendicular to an axis of vibration for generating ultrasonic shockwaves to emulsify or fracture tissue from vibratory motion of the ultrasonic frequency generator, wherein the cannula includes slits in fluid communication with the channel for suctioning in tissue to be emulsified or fractured and providing an outlet for irrigation solution, wherein each of the plurality of longitudinal fins has a height that extends from a center of the shaft to a periphery of the shaft.

15. The apparatus of claim 14, wherein the shaft includes three or four substantially straight longitudinal fins, with the substantially straight longitudinal fins equally spaced from each other.

16. An apparatus for removing tissue from a target zone of a patient, the apparatus comprising:

a shaft with a distal end and a proximal end, the proximal end removably attachable to an ultrasonic frequency generator positioned in a cavity of a handpiece and the shaft formed by a plurality of fins extending continuously from the proximal end portion of the shaft to the distal end of the shaft; and a cannula extending from the handpiece with a distal end and a proximal end, the proximal end removably attachable to the handpiece or the ultrasonic frequency generator and at least a portion of the shaft enclosed by the cannula, wherein activation of the ultrasonic frequency generator transmits vibratory energy through the shaft from the proximal end of the shaft to the distal end of the shaft to emulsify or fracture tissue, wherein a space between a lumen of the cannula and the plurality of fins of the shaft provides a channel for at least one of removing emulsified or fractured tissue from the cannula distal end through suction from a suction source and delivering irrigation solution to the cannula distal end from an irrigation solution source, and wherein each of the plurality of fins has a height that extends from a center of the shaft to a periphery of the shaft.

17. The apparatus of claim 16, wherein the plurality of fins of the shaft includes protrusions that are configured, dimensioned, and arranged to generate ultrasonic shockwaves to emulsify or fracture tissue.

18. The apparatus of claim 16, wherein the shaft includes three or four fins, with the fins equally spaced from each other.

19. The apparatus of claim 16, wherein the distal end of the shaft extends past the distal end of the cannula.

20. The apparatus of claim 16, wherein the shaft is a solid shaft without a lumen and each of the plurality of fins is substantially straight.

* * * * *